US006602672B1

(12) United States Patent
Prusiner et al.

(10) Patent No.: US 6,602,672 B1
(45) Date of Patent: Aug. 5, 2003

(54) RECOMBINANT CONSTRUCT ENCODING EPITOPE TAGGED PRP PROTEIN

(75) Inventors: Stanley B. Prusiner, San Francisco, CA (US); Glenn C. Telling, San Francisco, CA (US); Fred E. Cohen, San Francisco, CA (US); Michael R. Scott, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 25 days.

(21) Appl. No.: 09/669,516

(22) Filed: Sep. 25, 2000

Related U.S. Application Data

(63) Continuation of application No. 09/031,168, filed on Feb. 26, 1998, now Pat. No. 6,150,583, which is a division of application No. 08/660,626, filed on Jun. 6, 1996, now Pat. No. 5,789,655, which is a continuation-in-part of application No. 08/521,992, filed on Aug. 31, 1995, now Pat. No. 5,908,969, which is a continuation-in-part of application No. 08/509,261, filed on Jul. 31, 1995, now Pat. No. 5,763,740, which is a continuation-in-part of application No. 08/242,188, filed on May 13, 1994, now Pat. No. 5,565,186.

(51) Int. Cl.[7] .......................... G01N 33/53; C12P 21/06; C07H 21/02; C07K 14/00

(52) U.S. Cl. ..................... 435/7.1; 435/69.1; 435/320.1; 435/325; 435/252.3; 536/23.1; 530/350

(58) Field of Search .................. 536/23.1; 435/325, 435/252.3, 320.1, 7.1, 69.1; 530/350

(56) References Cited

U.S. PATENT DOCUMENTS

| 4,873,191 A | 10/1989 | Wagner et al. |
|---|---|---|
| 5,487,992 A | 1/1996 | Capecchi et al. |
| 5,545,808 A | 8/1996 | Hew et al. |
| 5,554,512 A | 9/1996 | Lyman et al. |
| 5,565,186 A | 10/1996 | Prusiner et al. |
| 5,789,655 A | 8/1998 | Prusiner et al. |

FOREIGN PATENT DOCUMENTS

| WO | WO 94/16092 | 7/1994 |
|---|---|---|
| WO | WO 95/20666 | 8/1995 |
| WO | WO 95/31466 | 11/1995 |

OTHER PUBLICATIONS

Basler, K., et al., (1986) "Scrapie and cellular PrP isoforms are encoded by the same chromosmal gene", *Cell* 46:417–428.

Bolton, D.C., et al., (1982) "Identification of a protein that purifies with the scrapie prion", *Science vol.* 218:1309–1311.

Borchelt, D.R., et al., (1990) "Scrapie and cellular prion proteins differ in their kinetics of synthesis and topology in cultured cells." *J. Cell Biol.* 110:743–52.

Bueler, H., et al., (1992) "Normal development and behavior of mice lacking the neuronal cell–surface PrP protein", *Nature* 356.

Gabriel, J.–M., et al., (1992) "Molecular cloning of a candidate chicken prion protein", *Proc. Natl. Acad. Sci. USA* 89:9097–9101.

Hecker, R., et al., "Replication of distinct scarpie prion isolates is region specific in brains of transgenic mice and hamsters", *Genes and Development* 6:1213–1228.

Houdebine, Louis–Marie, (1994), "Production of Pharmaceutical Proteins from Transgenic Animals", *J. of Biotechnology* 34:269–287.

Kascsak, R.J., et al., (1987) "Mouse polyclonal and monoclonal antibody to scrapie–associated fibril proteins", *J. Virol.* 61:3688–93.

Knappik, A., and Pluckthun, A., (1994) "An improved affinity tag based on the FLAG peptide for the detection and purification of recombinant antibody fragments", *Biotechniques* 17:754–61.

Kunz, D., et al., (1992) "The human leukocyte platelet–activating factor receptor", *J. Biol. Chem.* 267:9101–6.

McKinley, P., et al., (1983) "A protease–resistant protein is a structural component of the scrapie prion", *Cell* 36:57–62.

Murray, P.J., et al., (1995) "Epitope tagging of the human endoplasmic reticulum HSP70 protein, BiP, to facilitate Analysis of BiP–substrate interactions", *Anal Biochem.* 229:170–9.

Pan, K.–M., et al., (1993) "Conversion of α–helicies into β–sheets features in the formation of the scrapie prion proteins", *Proc. Natl. Acad. Sci. USA* 90:10962–6.

Prusiner, et al., (1993) "Ablation of the Prion Protein (PrP) Gene in Mice Prevents Scrapie and Facilitates Production of Anti–PrP Antibodies", *Proc. Natl. Acad. Sci. USA* 90:10608–12.

Prusiner, S.B., et al., (1991) "Molecular Biology of prion diseases", *Sciences* 252:1515–1522.

Pursel, et al., (1989) "Genetic Engineering Livestock", *Science* 244:1281–8.

Ruoslahti, E., and Pierschbacher, M.D., (1987) "New perspectives in cell adhesion: RGD and integrins", *Science* 238:491–7.

Salter, et al., (1987) "Transgenic Chickens: Insertion of Retroviral Genes into the Chicken Germ Line", *Virol.* 157:236–40.

(List continued on next page.)

Primary Examiner—Karen Cochrane Carlson
(74) Attorney, Agent, or Firm—Karl Bozicevic; Bozicevic, Field & Francis LLP

(57) ABSTRACT

DNA constructs are provided of epitope-tagged proteins or protein fragments which are conveniently purified with immunoaffinity chromatography such as epitope-tagged prion proteins (PrP). Transgenic animals expressing an epitope-tagged protein are provided, including transgenic animals expressing epitope-tagged PrP. Methods for distinguishing between the conformational shapes of a protein and a convenient method for isolating a tagged protein by immunoaffinity chromatographic methods are provided.

18 Claims, 6 Drawing Sheets

OTHER PUBLICATIONS

Schmidt, T.G.M., and Skerra, A., (1994) "One–step affinity purification of bacterially produced proteins by means of the "Strep tag" and immobilized recombinant core streptavidin", *J. Chromatography 676*:337–45.

Scott, M.R., et al., (1989) "Chimeric prion protein expression in cultured cells and transgenic mice", *Cell 59*:847–57.

Scott, M., et al., (1992) "Transgenic mice expressing hamster prion protein produce species–specific scrapie infectivity and amyloid plaques", *Protein Sci. 1*:986–997.

Telling, G.C., et al., (1995) "Prion propagation in mice expressing human and chimeric PrP transgenes implicates the interaction of cellular PrP with another protein", *Cell 83*:79–90.

Telling et al., (1994) "Transmission of Creutzfeldt–Jakob Disease from Humans to Transgenic Mice Expressing Chimeric Human–Mouse Prion Protein", *Proc. Natl. Acad. Sci. USA 91*:9936–40.

Westway. D., et al., (1994) "Degeneration of Skeletal Muscle, Peripheral Nerves, and the Central Nervous system in transgenic mice overexpressing wild–type prion proteins", *Cell 76*:117–29.

FIG. 1

```
Mo  Met Ala Asn Leu Gly Tyr Trp Leu Leu Ala Leu Phe Val Thr Met Trp  16
Hu                          Cys     Met     Val             Ala Thr

Mo  Thr Asp Val Gly Leu Cys Lys Lys Arg Pro Lys Pro Gly Gly Trp Asn  32
Hu  Ser     Leu

Mo  Thr Gly Gly Ser Arg Tyr Pro Gly Gln Gly Ser Pro Gly Gly Asn Arg  48
Hu

Mo  Tyr Pro Pro Gln Gly Gly --- Thr Trp Gly Gln Pro His Gly Gly Gly  63
Hu                          Gly Gly

Mo  Trp Gly Gln Pro His Gly Gly Ser Trp Gly Gln Pro His Gly Gly Ser  79
Hu                              Gly                                 Gly

Mo  Trp Gly Gln Pro His Gly Gly Gly Trp Gly Gln Gly Gly Gly Thr His  95
Hu

Mo  Asn Gln Trp Asn Lys Pro Ser Lys Pro Lys Thr Asn Leu Lys His Val  111
Hu  Ser                                              Met         Met

Mo  Ala Gly Ala Ala Ala Ala Gly Ala Val Val Gly Gly Leu Gly Gly Tyr  127
Hu

Mo  Met Leu Gly Ser Ala Met Ser Arg Pro Met Ile His Phe Gly Asn Asp  143
Hu                                      Ile                     Ser

Mo  Trp Glu Asp Arg Tyr Tyr Arg Glu Asn Met Tyr Arg Tyr Pro Asn Gln  159
Hu  Tyr                                  His

Mo  Val Tyr Tyr Arg Pro Val Asp Gln Tyr Ser Asn Gln Asn Asn Phe Val  175
Hu                          Met     Glu

Mo  His Asp Cys Val Asn Ile Thr Ile Lys Gln His Thr Val Thr Thr Thr  191
Hu

Mo  Thr Lys Gly Glu Asn Phe Thr Glu Thr Asp Val Lys Met Met Glu Arg  207
Hu

Mo  Val Val Glu Gln Met Cys Val Thr Gln Tyr Gln Lys Glu Ser Gln Ala  223
Hu                          Ile             Glu Arg

Mo  Tyr Tyr Asp Gly Arg Arg Ser Ser Ser Thr Val Leu Phe Ser Ser Pro  239
Hu          Gln --- ---         Gly         Met

Mo  Pro Val Ile Leu Leu Ile Ser Phe Leu Ile Phe Leu Ile Val Gly      254
Hu
```
(SEQ ID NO: 8)
(SEQ ID NO: 7)

FIG. 2

```
Mo  Met Ala Asn Leu ---  --- Gly Tyr Trp Leu Leu Ala Leu Phe Val Thr  14
Bo      Val Lys Ser His  Ile     Ser     Ile     Val         Ala

Mo  Met Trp Thr Asp Val Gly Leu Cys Lys Lys Arg Pro Lys Pro Gly Gly  30
Bo          Ser

Mo  --- Trp Asn Thr Gly Gly Ser Arg Tyr Pro Gly Gln Gly Ser Pro Gly  45
Bo

Mo  Gly Asn Arg Tyr Pro Pro Gln Gly Gly --- Thr Trp Gly Gln Pro His  60
Bo                                      Gly     Gly

Mo  Gly Gly Gly Trp Gly Gln Pro His Gly Gly Ser Trp Gly Gln Pro His  76
Bo                                          Gly

Mo  Gly Gly Ser Trp Gly Gln Pro His Gly Gly Gly Trp Gly Gln --- ---  90
Bo          Gly                                             Pro His

Mo  --- --- --- --- --- --- Gly Gly Gly Thr His Asn Gln Trp Asn Lys 100
Bo  Gly Gly Gly Gly Trp Gly Gln                 Gly

Mo  Pro Ser Lys Pro Lys Thr Asn Leu Lys His Val Ala Gly Ala Ala Ala 116
Bo                              Met

Mo  Ala Gly Ala Val Val Gly Gly Leu Gly Gly Tyr Met Leu Gly Ser Ala 132
Bo

Mo  Met Ser Arg Pro Met Ile His Phe Gly Asn Asp Trp Glu Asp Arg Tyr 148
Bo              Leu                         Ser     Tyr

Mo  Tyr Arg Glu Asn Met Tyr Arg Tyr Pro Asn Gln Val Tyr Tyr Arg Pro 164
Bo                      His

Mo  Val Asp Gln Tyr Ser Asn Gln Asn Asn Phe Val His Asp Cys Val Asn 180
Bo

Mo  Ile Thr Ile Lys Gln His Thr Val Thr Thr Thr Thr Lys Gly Glu Asn 200
Bo              Val     Glu

Mo  Phe Thr Glu Thr Asp Val Lys Met Met Glu Arg Val Val Glu Gln Met 212
Bo                          Ile

Mo  Cys Val Thr Gln Tyr Gln Lys Glu Ser Gln Ala Tyr Tyr Asp Gly Arg 228
Bo                                                      Gln ---

Mo  Arg Ser Ser Ser Thr Val Leu Phe Ser Ser Pro Pro Val Ile Leu Leu 244
Bo  ---     Gly Ala     Val Ile

Mo  Ile Ser Phe Leu Ile Phe Leu Ile Val Gly                         254
Bo
(SEQ ID NO: 9)
(SEQ ID NO: 7)
```

FIG. 3

```
Mo  Met Ala Asn Leu ---  ---  Gly Tyr Trp Leu Leu Ala Leu Phe Val Thr  14
Sh      Val Lys Ser His  Ile      Ser     Ile     Val         Ala

Mo  Met Trp Thr Asp Val Gly Leu Cys Lys Lys Arg Pro Lys Pro Gly Gly  30
Sh          Ser

Mo  --- Trp Asn Thr Gly Gly Ser Arg Tyr Pro Gly Gln Gly Ser Pro Gly  45
Sh

Mo  Gly Asn Arg Tyr Pro Pro Gln Gly Gly --- Thr Trp Gly Gln Pro His  60
Sh                                      Gly Gly

Mo  Gly Gly Gly Trp Gly Gln Pro His Gly Gly Ser Trp Gly Gln Pro His  76
Sh                                              Gly

Mo  Gly Gly Ser Trp Gly Gln Pro His Gly Gly Gly --- Trp Gly Gln Gly  91
Sh                                              Gly

Mo  Gly Gly Thr His Asn Gln Trp Asn Lys Pro Ser Lys Pro Lys Thr Asn 107
Sh          Ser --- His Ser

Mo  Leu Lys His Val Ala Gly Ala Ala Ala Ala Gly Ala Val Val Gly Gly 123
Sh  Met

Mo  Leu Gly Gly Tyr Met Leu Gly Ser Ala Met Ser Arg Pro Met Ile His 139
Sh                                                          Leu

Mo  Phe Gly Asn Asp Trp Glu Asp Arg Tyr Tyr Arg Glu Asn Met Tyr Arg 155
Sh                      Tyr

Mo  Tyr Pro Asn Gln Val Tyr Tyr Arg Pro Val Asp Gln Tyr Ser Asn Gln 171
Sh

Mo  Asn Asn Phe Val His Asp Cys Val Asn Ile Thr Ile Lys Gln His Thr 187
Sh                                              Val

Mo  Val Thr Thr Thr Thr Lys Gly Glu Asn Phe Thr Glu Thr Asp Val Lys 203
Sh                                                          Ile

Mo  Met Met Glu Arg Val Val Glu Gln Met Cys Val Thr Gln Tyr Gln Lys 219
Sh  Ile                                     Ile                 Arg

Mo  Glu Ser Gln Ala Tyr Tyr Asp Gly Arg Arg Ser Ser Ser Thr Val Leu 235
Sh                          Gln --- ---     Gly Ala     Val Ile

Mo  Phe Ser Ser Pro Pro Val Ile Leu Leu Ile Ser Phe Leu Ile Phe Leu 251
Sh

Mo  Ile Val Gly                                                     254
Sh
    (SEQ ID NO:10)
    (SEQ ID NO: 7)
```

Generation of N-terminally located FLAG-tagged PrP constructs

MANLSYWLLALFVAMWTDVGLCKKKRPKPGGWN (SEQ ID NO: 14)

Signal peptidase cleavage site
PflMI
New StuI maintains 1° structure

SEQUENCE LISTING

```
<160> NUMBER OF SEQ ID NOS: 13

<210> SEQ ID NO 1
<211> LENGTH: 8
<212> TYPE: PRT
<213> ORGANISM: Artificial Sequence
<220> FEATURE:
<223> OTHER INFORMATION: FLAG peptide

<400> SEQUENCE: 1

Asp Tyr Lys Asp Asp Asp Asp Lys
 1               5

<210> SEQ ID NO 2
<211> LENGTH: 8
<212> TYPE: PRT
<213> ORGANISM: Artificial Sequence
<220> FEATURE:
<223> OTHER INFORMATION: FLAG peptide

<400> SEQUENCE: 2

Asp Tyr Lys Asp Glu Asp Asp Lys
 1               5

<210> SEQ ID NO 3
<211> LENGTH: 9
<212> TYPE: PRT
<213> ORGANISM: Artificial Sequence
<220> FEATURE:
<223> OTHER INFORMATION: Strep peptide

<400> SEQUENCE: 3

Ala Trp Arg His Pro Gln Phe Gly Gly
 1               5

<210> SEQ ID NO 4
<211> LENGTH: 6
<212> TYPE: PRT
<213> ORGANISM: Artificial Sequence
<220> FEATURE:
<223> OTHER INFORMATION: poly-histidine peptide

<400> SEQUENCE: 4

His His His His His His
 1               5

<210> SEQ ID NO 5
```

```
<211> LENGTH: 42
<212> TYPE: DNA
<213> ORGANISM: Artificial Sequence
<220> FEATURE:
<223> OTHER INFORMATION: synthesized oligonucleotide

<400> SEQUENCE: 5
ttggccgctt cttcttgtca tcgtcgtcct tgtagtcgca ga                            42

<210> SEQ ID NO 6
<211> LENGTH: 47
<212> TYPE: DNA
<213> ORGANISM: Artificial Sequence
<220> FEATURE:
<223> OTHER INFORMATION: synthesized oligonucleotide

<400> SEQUENCE: 6
cctctgcgac tacaaggacg acgatgacaa gaagaagcgg ccaaagc                      47

<210> SEQ ID NO 7
<211> LENGTH: 254
<212> TYPE: PRT
<213> ORGANISM: Mus musculus

<400> SEQUENCE: 7

Met Ala Asn Leu Gly Tyr Trp Leu Leu Ala Leu Phe Val Thr Met Trp
 1               5                  10                  15

Thr Asp Val Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Thr Trp Gly Gln Pro His Gly Gly Gly Trp
    50                  55                  60

Gly Gln Pro His Gly Gly Ser Trp Gly Gln Pro His Gly Gly Ser Trp
65                  70                  75                  80

Gly Gln Pro His Gly Gly Gly Trp Gly Gln Gly Gly Thr His Asn
                85                  90                  95

Gln Trp Asn Lys Pro Ser Lys Pro Lys Thr Asn Leu Lys His Val Ala
            100                 105                 110

Gly Ala Ala Ala Ala Gly Ala Val Val Gly Gly Leu Gly Gly Tyr Met
        115                 120                 125

Leu Gly Ser Ala Met Ser Arg Pro Met Ile His Phe Gly Asn Asp Trp
    130                 135                 140

Glu Asp Arg Tyr Tyr Arg Glu Asn Met Tyr Arg Tyr Pro Asn Gln Val
145                 150                 155                 160

Tyr Tyr Arg Pro Val Asp Gln Tyr Ser Asn Gln Asn Phe Val His
                165                 170                 175

Asp Cys Val Asn Ile Thr Ile Lys Gln His Thr Val Thr Thr Thr Thr
            180                 185                 190

Lys Gly Glu Asn Phe Thr Glu Thr Asp Val Lys Met Met Glu Arg Val
        195                 200                 205

Val Glu Gln Met Cys Val Thr Gln Tyr Gln Lys Glu Ser Gln Ala Tyr
    210                 215                 220

Tyr Asp Gly Arg Arg Ser Ser Thr Val Leu Phe Ser Ser Pro Pro
225                 230                 235                 240

Val Ile Leu Leu Ile Ser Phe Leu Ile Phe Leu Ile Val Gly
                245                 250
```

```
<210> SEQ ID NO 8
<211> LENGTH: 253
<212> TYPE: PRT
<213> ORGANISM: Homo sapiens

<400> SEQUENCE: 8

Met Ala Asn Leu Gly Cys Trp Met Leu Val Leu Phe Val Ala Thr Trp
 1               5                  10                  15

Ser Asp Leu Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Gly Trp Gly Gln Pro His Gly Gly Gly
 50                  55                  60

Trp Gly Gln Pro His Gly Gly Gly Trp Gly Gln Pro His Gly Gly Gly
 65                  70                  75                  80

Trp Gly Gln Pro His Gly Gly Gly Trp Gly Gln Gly Gly Gly Thr His
                85                  90                  95

Ser Gln Trp Asn Lys Pro Ser Lys Pro Lys Thr Asn Met Lys His Met
                100                 105                 110

Ala Gly Ala Ala Ala Ala Gly Ala Val Val Gly Gly Leu Gly Gly Tyr
            115                 120                 125

Met Leu Gly Ser Ala Met Ser Arg Pro Ile Ile His Phe Gly Ser Asp
        130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Glu Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Ile Thr Gln Tyr Glu Arg Glu Ser Gln Ala
    210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250

<210> SEQ ID NO 9
<211> LENGTH: 263
<212> TYPE: PRT
<213> ORGANISM: bovine sp.

<400> SEQUENCE: 9

Met Val Lys Ser His Ile Gly Ser Trp Ile Leu Val Leu Phe Val Ala
 1               5                  10                  15

Met Trp Ser Asp Val Gly Leu Cys Lys Lys Arg Pro Lys Pro Gly Gly
            20                  25                  30

Trp Asn Thr Gly Gly Ser Arg Tyr Pro Gly Gln Gly Ser Pro Gly Gly
        35                  40                  45

Asn Arg Tyr Pro Pro Gln Gly Gly Gly Trp Gly Gln Pro His Gly
 50                  55                  60

Gly Gly Trp Gly Gln Pro His Gly Gly Gly Trp Gly Gln Pro His Gly
 65                  70                  75                  80

Gly Gly Trp Gly Gln Pro His Gly Gly Gly Trp Gly Gln Pro His Gly
```

```
                        85                   90                        95
Gly Gly Gly Trp Gly Gln Gly Thr His Gly Gln Trp Asn Lys Pro
                100                 105                 110
Ser Lys Pro Lys Thr Asn Met Lys His Val Ala Gly Ala Ala Ala
            115                 120                 125
Gly Ala Val Val Gly Leu Gly Gly Tyr Met Leu Gly Ser Ala Met
130                 135                 140
Ser Arg Pro Leu Ile His Phe Gly Ser Asp Tyr Glu Asp Arg Tyr Tyr
145                 150                 155                 160
Arg Glu Asn Met His Arg Tyr Pro Asn Gln Val Tyr Tyr Arg Pro Val
                165                 170                 175
Asp Gln Tyr Ser Asn Gln Asn Phe Val His Asp Cys Val Asn Ile
            180                 185                 190
Thr Val Lys Glu His Thr Val Thr Thr Thr Lys Gly Glu Asn Phe
            195                 200                 205
Thr Glu Thr Asp Ile Lys Met Met Glu Arg Val Val Glu Gln Met Cys
    210                 215                 220
Val Thr Gln Tyr Gln Lys Glu Ser Gln Ala Tyr Tyr Asp Gln Gly Ala
225                 230                 235                 240
Ser Val Ile Leu Phe Ser Ser Pro Val Ile Leu Ile Ser Phe
                245                 250                 255
Leu Ile Phe Leu Ile Val Gly
                260

<210> SEQ ID NO 10
<211> LENGTH: 255
<212> TYPE: PRT
<213> ORGANISM: ovine sp.

<400> SEQUENCE: 10

Met Val Lys Ser His Ile Gly Ser Trp Ile Leu Val Leu Phe Val Ala
1               5                   10                  15
Met Trp Ser Asp Val Gly Leu Cys Lys Lys Arg Pro Lys Pro Gly Gly
            20                  25                  30
Trp Asn Thr Gly Gly Ser Arg Tyr Pro Gly Gln Gly Ser Pro Gly Gly
        35                  40                  45
Asn Arg Tyr Pro Pro Gln Gly Gly Gly Trp Gly Gln Pro His Gly
50                  55                  60
Gly Gly Trp Gly Gln Pro His Gly Gly Gly Trp Gly Gln Pro His Gly
65                  70                  75                  80
Gly Ser Trp Gly Gln Pro His Gly Gly Gly Trp Gly Gln Gly Gly
                85                  90                  95
Ser His Ser Gln Trp Asn Lys Pro Ser Lys Pro Lys Thr Asn Met Lys
                100                 105                 110
His Val Ala Gly Ala Ala Ala Gly Ala Val Val Gly Gly Leu Gly
            115                 120                 125
Gly Tyr Met Leu Gly Ser Ala Met Ser Arg Pro Leu Ile His Phe Gly
130                 135                 140
Asn Asp Tyr Glu Asp Arg Tyr Tyr Arg Glu Asn Met Tyr Arg Tyr Pro
145                 150                 155                 160
Asn Gln Val Tyr Tyr Arg Pro Val Asp Gln Tyr Ser Asn Gln Asn Asn
                165                 170                 175
Phe Val His Asp Cys Val Asn Ile Thr Val Lys Gln His Thr Val Thr
            180                 185                 190
```

```
Thr Thr Thr Lys Gly Glu Asn Phe Thr Glu Thr Asp Ile Lys Ile Met
        195                 200                 205

Glu Arg Val Val Glu Gln Met Cys Ile Thr Gln Tyr Gln Arg Glu Ser
        210                 215                 220

Gln Ala Tyr Tyr Gln Arg Gly Ala Ser Val Ile Leu Phe Ser Ser Pro
225                 230                 235                 240

Pro Val Ile Leu Leu Ile Ser Phe Leu Ile Phe Leu Ile Val Gly
                245                 250                 255

<210> SEQ ID NO 11
<211> LENGTH: 13
<212> TYPE: PRT
<213> ORGANISM: Influenza virus

<400> SEQUENCE: 11

Tyr Pro Tyr Asp Val Pro Asp Tyr Ala Ile Glu Gly Arg
1               5                   10

<210> SEQ ID NO 12
<211> LENGTH: 11
<212> TYPE: PRT
<213> ORGANISM: Homo sapiens

<400> SEQUENCE: 12

Glu Gln Lys Leu Leu Ser Glu Glu Asp Leu Asn
1               5                   10

<210> SEQ ID NO 13
<211> LENGTH: 42
<212> TYPE: DNA
<213> ORGANISM: Artificial Sequence
<220> FEATURE:
<223> OTHER INFORMATION: synthesized oligonucleotide

<400> SEQUENCE: 13
ccctccaggc tttggccgct tcttgcagag gcctacatca gt          42
```

RECOMBINANT CONSTRUCT ENCODING EPITOPE TAGGED PRP PROTEIN

CROSS REFERENCES

This application is a continuation application of Ser. No. 09/031,168, filed Feb. 26, 1998 now issued as U.S. Pat. No. 6,150,583, which is a divisional application of Ser. No. 08/660,626, filed Jun. 6, 1996, and now issued as U.S. Pat. No. 5,789,655, issued Aug. 4, 1998, which is a continuation-in-part application of Ser. No. 08/521,992, filed Aug. 31, 1995, now issued as U.S. Pat. No. 5,908,969, issued Jun. 1, 1999 which is a continuation-in-part of Ser. No. 08/509,261, filed Jul. 31, 1995, now issued as U.S. Pat. No. 5,763,740, issued Jun. 9, 1998, which is a continuation-in-part application of Ser. No. 08/242,188, filed May 13, 1994, and now issued as U.S. Pat. No. 5,565,186, issued Aug. 15, 1996, all of which are incorporated herein by reference in their entirety and to which applications we claim priority under 35 U.S.C. §120.

STATEMENT AS TO FEDERALLY SPONSORED RESEARCH

The United States Government may have certain rights in this application pursuant to Grant Nos. NS14069, NS22786, AG02132, AG08967, AG10770 and NS07219 awarded by the National Institutes of Health.

FIELD OF THE INVENTION

This invention relates generally to epitope-tagged proteins and to transgenic animals expressing such proteins. More specifically, this invention relates to epitope-tagged prion protein (PrP) genes, transgenic animals expressing epitope-tagged PrP genes, and assay.methods for distinguishing between and isolating infectious and noninfectious prion proteins.

BACKGROUND OF THE INVENTION

Prions are infectious pathogens that cause central nervous system spongiform encephalopathies in humans and animals. Prions are distinct from bacteria, viruses and viroids. The predominant hypothesis at present is that no nucleic acid component is necessary for infectivity of prion protein. Further, a prion which infects one species of animal (e.g., a human) will not infect another (e.g., a mouse).

A major step in the study of prions and the diseases that they cause was the discovery and purification of a protein designated prion protein ("PrP") (Bolton et al. (1982) Science 218:1309–11; Prusiner et al. (1982) Biochemistry 21:6942–50; McKinley et al. (1983) Cell 35:57–62). Complete prion protein-encoding genes have since been cloned, sequenced and expressed in transgenic animals. $PrP^C$ is encoded by a single-copy host gene (Basler et al. (1986) Cell 46:417–28) and is normally found at the outer surface of neurons. A leading hypothesis is that prion diseases result from conversion of $PrP^C$ into a modified scrapie isoform called $PrP^{Sc}$ during a post-translational process (Borchelt et al. (1990) J. Cell Biol. 110:743–752). It is likely that a fundamental event in the propagation of prions is the conformational transition of alpha-helices in $PrP^C$ into beta-sheets in $PrP^{Sc}$ (Pan et al. (1993) Proc. Natl. Acad. Sci. 90:10962–10966). Genetic evidence from transgenic mouse studies demonstrates the requirement for an additional component(s) referred to as protein X in this conversion (Telling et al. (1995) Cell 83:79–90).

It appears that $PrP^{Sc}$ is necessary for both the transmission and pathogenesis of the transmissible neurodegenerative diseases of animals and humans (see, Prusiner (1991) Science 252:1515–1522). The most common prion diseases of animals are scrapie of sheep and goats and bovine spongiform encephalopathy (BSE) of cattle (Wilesmith & Wells (1991) Microbiol. Immunol. 172:21–38). Four prion diseases of humans have.been identified: (1) kuru, (2) Creutzfeldt-Jakob Disease (CJD), (3) Gerstmann-Strassler-Scheinker Disease (GSS), and (4) fatal familial insomnia (FFI) (Gajdusek (1977) Science 197:943–960; Medori et al. (1992) N. Engl. J. Med. 326:444–449). The presentation of human prion diseases as sporadic, genetic and infectious illnesses initially posed a conundrum which has been explained by the cellular genetic origin of PrP.

Most CJD cases are sporadic, but about 10–15% are inherited as autosomal dominant disorders that are caused by mutations in the human PrP gene (Hsiao et al. (1990) Neurology 40:1820–1827; Goldfarb et al. (1992) Science 258:806–808); Kitamoto et al. (1994) Proc. R. Soc. Lond. 343:391–398). Iatrogenic CJD has been caused by human growth hormone derived from cadaveric pituitaries as well as dura mater grafts (Brown et al. (1992) Lancet 340:24–27). attempts to link CJD to an infectious source such as the consumption of scrapie infected sheep meat, none has been identified to date (Harries-Jones et al. (1988) J. Neurol. Neurosurg. Psychiatry 51:1113–1119) except in cases of iatrogenically induced disease. On the other hand, kuru, which for many decades devastated the Fore and neighboring tribes of the New Guinea highlands, is believed to have been spread by infection during ritualistic cannibalism (Alpers (1979) Slow Transmissible Diseases of the Nervous System, Vol. 1, S. B. Prusiner and W. J. Hadlow, eds. (New York: Academic Press), pp. 66–90).

The initial transmission of CJD to experimental primates has a rich history beginning with William Hadlow's recognition of the similarity between kuru and scrapie. In 1959, Hadlow suggested that extracts prepared from patients dying of kuru be inoculated into non-human primates and that the animals be observed for disease that was predicted to occur after a prolonged incubation period (Hadlow (1959) Lancet 2:289–290). Seven years later, Gajdusek, Gibbs and Alpers demonstrated the transmissibility of kuru to chimpanzees after incubation periods ranging from 18 to 21 months (Gajdusek et al. (1966) Nature 209:794–796). The similarity of the neuropathology of kuru with that of CJD (Klatzo et al. (1959) Lab Invest. 8:799–847) prompted similar experiments with chimpanzees and transmissions of disease were reported in 1968 (Gibbs, Jr. et al. (1968) Science 161:388–389). Over the last 25 years, about 300 cases of CJD, kuru and GSS have been transmitted to a variety of apes and monkeys.

The expense, scarcity and often perceived inhumanity of such experiments have restricted this work and thus limited the accumulation of knowledge. While the most reliable transmission data has been said to emanate from studies using non-human primates, some cases of human prion disease have been transmitted to rodents but apparently with less regularity (Gibbs, Jr. et al. (1979) Slow Transmissible Diseases of the Nervous System, Vol. 2, S. B. Prusiner and W. J. Hadlow, eds. (New York: Academic Press), pp. 87–110; Tateishi et al. (1992) Prion Diseases of Humans and Animals, Prusiner et al., eds. (London: Ellis Horwood), pp. 129–134).

The infrequent transmission of human prion disease to rodents has been cited as an example of the "species barrier" first described by Pattison in his studies of passaging the scrapie agent between sheep and rodents (Pattison (1965) NINDB Monograph 2, D. C. Gajdusek, C. J. Gibbs Jr. and M. P. Alpers, eds. (Washington, D.C.: U.S. Government Printing), pp. 249–257). In those investigations, the initial passage of prions from one species to another was associated with a prolonged incubation time with only a few animals developing illness. Subsequent passage in the same species was characterized by all the animals becoming ill after greatly shortened incubation times.

The molecular basis for the species barrier between Syrian hamster (SHa) and mouse (Mo) was shown to reside in the species-specific differences in the sequence of the PrP (Scott et al. (1989) Cell 59:847–857). Mouse PrP (MoPrP) differs from Syrian hamster PrP (SHaPrP) at 16 positions out of 254 amino acid residues (Basler et al. (1986), Cell supra; Locht et al. (1986) Proc. Natl. Acad. Sci. USA 83:6372–6376). Transgenic mice expressing SHaPrP [Tg (SHaPrP)] had abbreviated incubation times when inoculated with SHa prions. When similar studies were performed with mice expressing the human, or ovine PrP transgenes, the species barrier was not abrogated, i.e., the percentage of animals which became infected were unacceptably low and the incubation times were unacceptably long (Telling et al. (1994) Proc. Natl. Acad. Sci. 91:9936–9940; Telling et al. (1995) Cell 83:79–90). Thus, it was not possible to render non-human animals such as mice, susceptible to infection by human prions.

Purification of PrP$^{Sc}$ has been facilitated by its relative resistance to proteolytic degradation and insolubility in non-denaturing detergents (Bolton et al. (1982) supra; Prusiner et al. (1982) supra. Purification of PrP$^{C}$ has been more problematic. Immunoaffinity chromatography purification of PrP$^{C}$ yielded only small amounts of protein. Improved purification of PrP$^{C}$ has been accomplished by a multi-step purification procedure involving detergent extraction and separation by immobilized $Cu^{2+}$ ion affinity chromatography followed by cation-exchange chromatography and sodium dodecyl sulfate-polyacrylamide gel electrophoresis (SDS-PAGE) (Pan et al. (1992) Protein Sci. 1:136–144).

The production of monoclonal antibodies against PrP$^{C}$ and PrP$^{Sc}$ has been particularly difficult. In the case of mouse PrP, MoPrP is recognized as self, precluding the production of anti-MoPrP antibodies in animals immunized with MoPrP.

There is an urgent need to develop diagnostics and therapeutics for PrP$^{Sc}$-mediated diseases such as CJD. Although many lines of evidence support the idea that PrP$^{C}$ is converted to the infectious PrP$^{Sc}$ isoform, greater understanding of the conditions under which scrapie infectivity is generated de novo is needed to develop compounds able to inhibit the generation of PrP$^{Sc}$. Compounds able to inhibit the in vitro conversion of PrP$^{C}$ to PrP$^{Sc}$ could be useful for the treatment and prevention of prion-mediated diseases in animal and human subjects at risk. Improved methods for monitoring the conversion of PrP from the alpha-helical conformation of PrP$^{C}$ to the beta-sheet conformation of the infectious PrP$^{Sc}$ isoform would be useful in developing assays for such compounds.

SUMMARY OF THE INVENTION

Nucleotides encoding a strong epitope tag are operatively placed in a nucleotide sequence encoding a protein which normally has two or more conformational shapes. Depending on the conformational shape assumed by the expressed protein, the tag will or will not be exposed thereby making it possible to differentiate between conformational shapes via an antibody which binds to the epitope. An aspect of the invention features a recombinant nucleic acid construct comprising a nucleic acid sequence encoding an amino acid sequence comprising a biologically active protein or protein fragment connected, preferably directly, to a heterologous epitope domain. The expressed amino acid sequence (i.e., the epitope-tagged protein) preferably retains the biological activity of the corresponding natural (e.g., untagged) protein or protein fragment. The tag may be used in connection with a protein which has two or more different conformational shapes, such that the epitope tag is relatively more exposed in one conformational shape relative to another conformational shape.

One aspect of the invention is a transgenic animal such as a mouse which has incorporated into its genome a first DNA sequence encoding a protein which when expressed assumes two or more different conformational shapes. The first DNA sequence has a second DNA sequence encoding an epitope tag connected to it. The second sequence is preferably positioned relative to the first sequence such that the exposure of the tag after expression changes with the different conformational shapes assumed by the protein expressed by the first sequence. The first DNA sequence is preferably an exogenous sequence which encodes a protein such as PrP which protein causes a disease in one conformational shape but not another. Thus by correctly positioning the second sequence encoding the tag relative to the first sequence, it is possible to quickly and easily assay a sample from the animal and determine which conformation the protein has assumed.

Transgenic mammals comprising a tagged transgene are preferably selected from the group consisting of Mus, Rattus, Oryctolagus and Mesocricetus. Transgenic animals expressing high levels of the tagged transgene may be obtained, for example, by over-expression of the transgene with an enhanced promoter and/or with high copy numbers of the transgene.

In a specific embodiment, the invention features a transgenic mammal having an epitope-tagged PrP gene. The PrP gene may be a natural, synthetic, or chimeric PrP gene. In specific embodiments, the transgenic animals have an epitope-tagged chimeric PrP gene which renders the transgenic animals susceptible to infection with a prion which generally only infects a genetically diverse or distinct animal. A chimeric PrP gene is a gene which includes a portion of a gene of a genetically diverse animal. When the transgenic animal is a one of Mus, Rattus, Oryctolagus, or Mesocricetus, the genetically diverse or distinct animal is selected from the group consisting of Bos, Ovis, Sus, and Homo. A preferred transgenic animal is a mouse expressing a epitope-tagged chimeric PrP in which a segment of mouse (Mo) PrP is replaced with the corresponding human (Hu) PrP sequence.

The transgenic animal may be heterozygous or homozygous for an ablated or disrupted endogenous PrP gene; in a preferred embodiment, the transgenic animal is homozygous for an ablated endogenous PrP gene.

In a preferred embodiment of the invention, the epitope-tagged protein is a natural, synthetic, or chimeric prion protein (PrP). PrP may be tagged with a variety of natural or artificial heterologous epitopes known in the art, including artificial epitopes such as FLAG, Strep, or poly-histidine peptides. FLAG peptides include the sequence Asp-Tyr-Lys-Asp-Asp-Asp-Asp-Lys (SEQ ID NO:1) or Asp-Tyr-Lys-Asp-Glu-Asp-Asp-Lys (SEQ ID NO:2). The Strep epitope has the sequence Ala-Trp-Arg-His-Pro-Gln-Phe-Gly-Gly (SEQ ID NO:3). Another commonly used artificial epitope is a poly-His sequence having six histidine residues (His-His-His-His-His-His) (SEQ ID NO:4). Naturally-occurring epitopes include the influenza virus hemagglutinin sequence Tyr-Pro-Tyr-Asp-Val-Pro-Asp-Tyr-Ala-Ile-Glu-Gly-Arg (SEQ ID NO:11) recognized by the monoclonal antibody 12CA5 (Murray et al. (1995) Anal. Biochem. 229:170–179) and the eleven amino acid sequence from human c-myc recognized by the monoclonal antibody 9E10 (Glu-Gln-Lys-Leu-Leu-Ser-Glu-Glu-Asp-Leu-Asn) (SEQ ID NO:12) (Manstein et al. (1995) Gene 162:129–134). Another useful epitope is the tripeptide Glu-Glu-Phe which is recognized by the monoclonal antibody YL 1/2 against α-tubulin. This tripeptide has been used as an affinity tag for the purification of recombinant proteins (Stammers et al. (1991) FEBS Lett. 283:298–302).

In a particularly preferred embodiment, the epitope tagged PrP molecule has an artificial FLAG epitope inserted after codon 22, e.g., the first codon of the FLAG epitope begins at codon 23 of a nucleotide sequence encoding a FLAG-tagged PrP protein. The FLAG-tagged PrP molecule retains all of the biological activity of the natural PrP molecule. Specifically, the FLAG-tagged PrP protein retains the ability to support prion propagation.

The invention further includes cells, e.g., omnipotent and pluripotent cells, and immortalized cell lines expressing the epitope-tagged protein construct, as well as transgenic animals having a gene encoding an epitope-tagged protein integrated into their genome.

In another aspect, the invention features a method for distinguishing between the conformational shapes of a protein having a first and second conformation shape, comprising the steps of: (a) generating a recombinant nucleic acid construct comprising a nucleic acid sequence encoding an amino acid sequence comprising a protein fragment tagged with a heterologous epitope; b) transfecting a cell or organism with the tagged protein construct; c) expressing the tagged protein. The epitope tag is positioned relative to the protein sequence such that the epitope is exposed on the surface of the tagged protein to a greater degree when the protein is in a first conformational shape relative to the degree of exposure of the epitope when the protein is in a second conformational shape. In one embodiment, the conformational shapes of the protein can be distinguished by detecting the presence or absence of the epitope. Multiple different tags can be used if the protein assumes multiple conformations, making it possible to distinguish the conformations via detection of the presence or absence of a series of tags. In another embodiment, the conformational shapes of a protein are distinguished by relatively greater exposure of the epitope tag in one conformational shape than in other conformational shapes. Preferably, the exposure of an epitope tag is 20–100% greater in one conformational shape relative to the second conformational shape; more preferably, the relative exposure is 50–100% greater; most preferably, the relative exposure is 75–100% greater.

In one embodiment, the epitope-tagged protein is PrP, and the epitope tag is placed such that it is unexposed on the surface of the expressed prion protein when it is in the noninfectious alpha-helical $PrP^C$ isoform, but the epitope tag is exposed on the surface of the infectious beta-sheet $PrP^{Sc}$ isoform.

In another aspect, the invention features a method of isolating PrP by a) generating a recombinant nucleic acid construct comprising a nucleic acid sequence encoding a prion protein having a heterologous epitope domain; b) transfecting a cell or organism with the tagged PrP construct; c) expressing the construct to produce epitope-tagged PrP, where the epitope tag is placed such that it is exposed on the surface of the desired PrP isoform; and d) purifying PrP by immunoaffinity chromatography using an anti-epitope tag antibody. In a specific embodiment, the method of isolating PrP includes an additional step of enriching for PrP prior to purification. This method can be used to isolate, separate and identify either $PrP^C$ and/or $PrP^{Sc}$.

In another aspect, the invention features an assay method for detecting infectious prions by a) generating a transgenic animal comprised of an epitope-tagged PrP gene where the epitope tag is relatively more exposed on the surface of the expressed PrP molecule when the molecule has the $PrP^{Sc}$ conformation than when the molecule is in the $PrP^C$ conformation; b) inoculating the transgenic animal with material suspected of containing infectious prions; and c) detecting the increased presence of epitope-tagged PrP. Detection of increased levels of epitope-tagged PrP results from increased levels of PrP in the infectious $PrP^{Sc}$ conformation, thus indicating the presence of infectious PrP particles in the inoculating material. In one preferred embodiment, the transgenic animal expresses a bovine-mouse MBov2M chimeric PrP gene and is inoculated with material from infected cattle. In another preferred embodiment, the transgenic animals expresses a chimeric human-mouse MHu2M PrP molecule and is inoculated from material from an infected human.

One object of the invention is to provide a transgenic animal producing large quantities of an epitope-tagged protein or protein fragment which is easily purified via immunoaffinity chromatography using an epitope-specific antibody. This is particularly useful where the protein is difficult to purify in sufficient quantities and/or attempts to produce antibodies specific to the protein and its conformation isoforms have been unsuccessful, e.g., $PrP^C$ and $PrP^{Sc}$. Additionally, the invention allows a simplified one-step enrichment of $PrP^C$ and/or $PrP^{Sc}$, which can be followed by a variety of procedures including immunodetection.

Another object is to provide a transgenic animal expressing elevated levels of a tagged protein or protein fragment obtained with an enhanced promoter or a high copy number of a tagged transgene.

Another object is to provide a method for distinguishing conformational changes in a protein, e.g., distinguishing between the isoforms of $PrP^C$ and $PrP^{Sc}$.

Another object is to provide a gene tagged with a heterologous epitope.

Another object of the invention is to provide a transgenic host mammal (which is small, e.g., less than 1 kg when full grown, and inexpensive to maintain) such as a mouse, rat or hamster which includes an exogenous or chimeric PrP gene, including all or a portion of a PrP gene from another animal, (which is large, greater than 2 kg when full grown, and expensive to maintain) such as a human, cow, pig, sheep, cat or dog, and having a artificial epitope tag domain.

Another object of the invention is to provide a transgenic host animal which includes elevated levels of expression of a tagged PrP gene of a genetically diverse animal wherein the elevated levels of expression are obtained by the inclusion of a high copy number of the tagged PrP gene of the genetically diverse mammal and/or fusing an enhanced promoter to the PrP gene of the genetically diverse animal.

One advantage of the method of the invention is the production of elevated levels of readily isolatable $PrP^C$ and $PrP^{Sc}$.

Another object is to provide a transgenic animal assay which animal, on inoculation, develops $PrP^{Sc}$ which is detectable via an epitope tag as distinguished from $PrP^C$.

These and other objects, advantages and features of the present invention will become apparent to those persons skilled in the art upon reading the details of the compositions, composition components, methods and method steps of the invention as set forth below.

BRIEF DESCRIPTION OF THE FIGURES

FIG. 1 shows the amino acid sequence of mouse PrP along with specific differences between mouse PrP and human PrP (SEQ ID NO:8).

FIG. 2 shows the amino acid sequence of mouse PrP (SEQ ID NO:7) along with specific differences between mouse PrP and bovine PrP (SEQ ID NO:9).

FIG. 3 shows the amino acid sequence of mouse PrP (SEQ ID NO:7) along with specific differences between mouse PrP and sheep PrP (SEQ ID NO:10).

DETAILED DESCRIPTION

Figure 4:
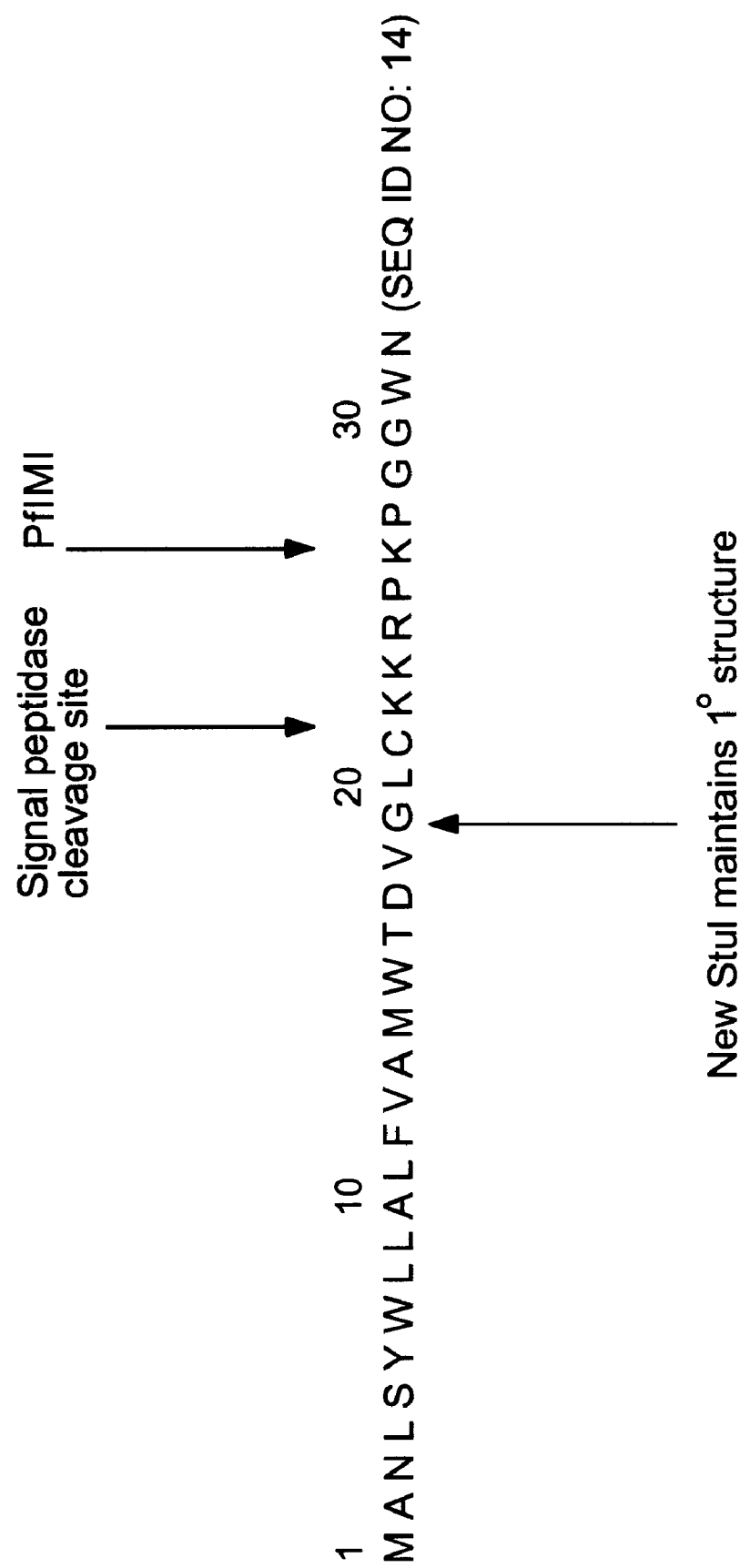
FIG. 4 is the PrP amino acid sequence showing insertion of a StuI recognition site upstream of the signal peptidase cleavage site at amino acid 2 (SEQ ID NO:14).

Before the present artificial epitope-tagged gene, assay methodology, and transgenic animals used in the assay are described, it is to be understood that this invention is not limited to particular assay methods, epitope-tagged and artificial genes, or transgenic animals described, as such methods, genes, and animals may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited. The publications discussed above are provided solely for their disclosure prior to the filing date of the present application. Nothing herein is to be construed as an admission that the invention is not entitled to antedate such disclosure by virtue of prior invention.

Definitions

The term "artificial" as used with "artificial gene" or "artificial epitope" and the like, refers to a non-naturally occurring material, e.g., a nucleotide sequence manufactured by human intervention, e.g., by fusing natural sequences together or chemically synthesizing sequences in isolation. Further, the term is intended to encompass a natural sequence which may be isolated from a naturally occurring genome and then connected, artificially, with an sequence (either a natural or artificial sequence) with which it is not naturally connected, e.g., a natural HIV virus epitope connected directly to a natural PrP sequence is expressed by an "artificial gene."

The term "transgene" or "transgenic element" refers to an artificially introduced, chromosomally integrated nucleic acid sequence heterologous to the genome of the host animal in which the nucleic acid sequence is present.

The term "transgenic animal" means a non-human mammalian animal having a transgenic element integrated in its genome.

The term "prion" means an infectious particle known to cause diseases (spongiform encephalobpathies) in humans and animals. The term "prion" is a contraction of the words "protein" and "infection" and the particles are comprised largely if not exclusively of PrP$^{Sc}$ molecules encoded by a PrP gene. Prions are distinct from bacteria, viruses and viroids. Known prions include those which infect animals to cause scrapie, a transmissible, degenerative disease of the nervous system of sheep and goats as well as bovine spongiform encephalopathies (BSE) or mad cow disease and feline spongiform encephalopathies of cats. Four prion diseases known to affect humans are (1) kuru, (2) Creutzfeldt-Jakob Disease (CJD), (3) Gerstmann-Strassler-Scheinker Disease (GSS), and (4) fatal familial insomnia (FFI). As used herein prion includes all forms of prions causing all or any of these diseases or others in any animals used—and in particular in humans and in domesticated farm animals.

The term "PrP gene", "prion protein gene" or "PrP sequence" are used interchangeably herein to describe genetic material which expresses any PrP proteins, for example those shown in FIGS. 1–3. There are a number of known variants to the human PrP gene. Further, there are known polymorphisms in the human, sheep, and bovine PrP gene. The following is a list of such variants:

| Pathogenic human mutations | Human Polymorphisms | Sheep Polymorphisms | Bovine Polymorphisms |
|---|---|---|---|
| 2 octarepeat insert | Codon 129 Met/Val | Codon 171 Arg/Glu | 5 or 6 octarepeat |
| 4 octarepeat insert | Codon 219 Glu/Lys | Codon 136 Ala/Val | |
| 5 octarepeat insert | | | |
| 6 octarepeat insert | | | |
| 7 octarepeat insert | | | |
| 8 octarepeat insert | | | |
| 9 octarepeat insert | | | |
| Codon 102 Pro-Leu | | | |
| Codon 105 Pro-Leu | | | |
| Codon 117 Ala-Val | | | |
| Codon 145 Stop | | | |
| Codon 178 Asp-Asn | | | |
| Codon 180 Val-Ile | | | |
| Codon 198 Phe-Ser | | | |
| Codon 200 Glu-Lys | | | |
| Codon 210 Val-Ile | | | |
| Codon 217 Asn-Arg | | | |

-continued

| Pathogenic human mutations | Human Polymorphisms | Sheep Polymorphisms | Bovine Polymorphisms |
|---|---|---|---|
| Codon 232 Met-Ala | | | |

The PrP gene can be a naturally-occurring PrP gene from any animal described herein and any and all polymorphisms and mutations thereof, it being recognized that the terms include other such PrP genes that are yet to be discovered. The term "PrP gene" generally includes any gene of any species which encodes any form of a prion protein. Some commonly known PrP sequences are described in Gabriel et al., *Proc. Natl. Acad. Sci. USA* 89:9097–9101 (1992) which is incorporated by reference to disclose and describe such sequences. Besides naturally-occurring PrP genes, the term "PrP gene" further encompasses artificial, synthetic, and chimeric Prp genes.

The term "chimeric PrP gene" is used herein to encompass recombinantly constructed genes which when included in the genome of a host animal (e.g., a mouse) will render the mammal susceptible to infection from prions which naturally only infect a genetically diverse test mammal, e.g., human, bovine or ovine. A chimeric PrP will accomplish this effect in an animal which includes an operative endogenous PrP gene and allow the animal to show symptoms within 200±50 days after inoculation. In general, a chimeric gene will include the codon sequence of the PrP gene of the mammal being genetically altered with one or more (but not all, and generally less than 40) codons of the natural sequence being replaced with a different codon—preferably a corresponding codon of a genetically diverse mammal (such as a human). The genetically altered mammal being used to assay samples for prions which only infect the genetically diverse mammal. Examples of artificial genes are mouse PrP genes encoding the sequence as shown in FIGS. 1, 2 and 3 with one or more different replacement cbdohs selected from the codons shown in these Figures for humans, cows and sheep replacing mouse codons at the same position, with the proviso that not all the mouse codons are replaced with differing human, cow or sheep codons. The chimeric PrP genes of the invention can include not only codons of genetically diverse animals but may include codons and codon sequences not associated with any native PrP gene but which, when inserted into an animal render the animal susceptible to infection with prions which would normally only infect a genetically diverse animal. The chimeric PrP genes can also include deletions of codons in the naturally-occurring gene of the host animal genome.

The terms "heterologous epitope domain" or "heterologous epitope tag" are used interchangeably to mean a peptide which does not naturally occur as part of the protein or protein fragment. The heterologous epitope may be a naturally-occurring or artificial peptide. Heterologous epitope tags are distinguished from naturally occurring antigenic PrP sequences to which monoclonal antibodies such as 3F4 and 13AS have been raised. The heterologous epitope tag does not necessarily have to be antigenic, e.g., generate a specific antibody. The epitope tag includes peptides bound by specific ligands. For example, an Arg-Gly-Asp sequence may be inserted into the PrP protein which binds integrins (Ruoslahti & Eierschbacher (1987) Science 238:491–497).

The term "heterologous epitope-tagged gene" or "tagged gene" are used to mean an artificially constructed nucleotide sequence comprising a gene (i.e., a first nucleotide sequence) encoding an amino acid sequence comprising a biologically active protein or protein fragment of interest and a second nucleotide sequences encoding an epitope tag which does not naturally occur as part of the protein or protein fragment, e.g., heterologous. The sequence encoding the tag may be placed 5', 3', and/or within the sequence encoding the protein of interest. Expression of the tagged gene results in production of a protein or protein fragment having one or more heterologous epitope domain(s).

The terms "epitope-tagged PrP gene" or "tagged PrP gene", and the like are used interchangeably herein to mean an artificially constructed gene containing the nucleotide sequence encoding the PrP protein of an animal such as a mouse, human, cow, or sheep and additionally containing nucleotide sequences encoding one or more epitope tags inserted into the PrP gene. Expression of the tagged PrP gene results in production of PrP molecule having one or more artificial epitope domain(s). In one specific example the tagged PrP gene is comprised of the nucleotide sequence encoding mouse PrP with a nucleotide sequence encoding an artificial FLAG epitope inserted at codon 22. In another specific embodiment, the tagged-PrP gene comprises the nucleotide sequence encoding chimeric mouse-hamster PrP (MHM2) with the nucleotide sequence encoding a FLAG epitope inserted at codon 22 of the MHM2 PrP gene. The nucleotide sequence also contains the epitope derived from hamster PrP recognized by the monoclonal antibody 3F4 (Scott et al. (1992) Protein Sci. 1:986–997). The resulting tagged PrP molecule can be readily purified through immunoaffinity methodologies with the use of antibodies to the epitope tag(s).

Figure 5:
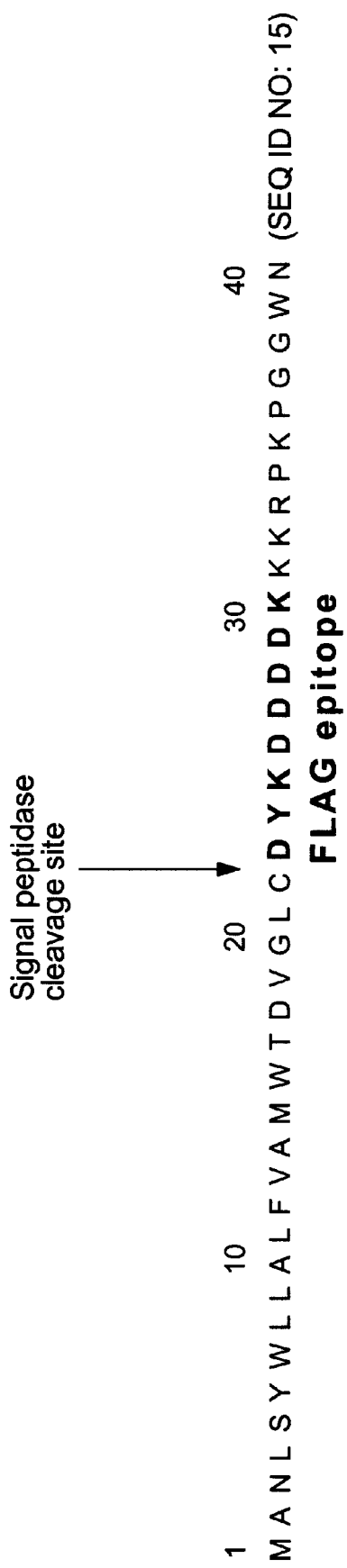
FIG. 5 is the amino acid sequence of tagged PrP having the FLAG epitope inserted at amino acid 2 (SEQ ID NO:15).

The terms "epitope-tagged chimeric PrP gene" or "tagged chimeric PrP gene", and the like are used interchangeably herein to mean an artificially constructed PrP gene containing the nucleotide sequence encoding the PrP protein of a host animal such as a mouse with one or more of the codons being replaced with corresponding codons from a genetically diverse test animal such as a human, cow or sheep, and having a nucleotide sequence encoding a heterologous epitope tag inserted into the PrP gene, such that expression of the tagged PrP gene results in production of a PrP protein having one or more heterologous epitope domain(s). In one specific example the tagged PrP gene is comprised of the starting and terminating sequence (i.e., N- and C-terminal codons) of a PrP gene of a mammal of a host species (e.g. a mouse), a nucleotide sequence of a corresponding portion of a PrP gene of a test mammal of a second species (e.g. a human), and a nucleotide sequence encoding a FLAG epitope at codon 22 (FIG. 5). When inserted into the genome of a mammal of the host species, the tagged PrP gene will render the mammal susceptible to infection with prions which normally infect only mammals of the second, genetically diverse, species, i.e, on inoculation the host animal will show symptoms of prion disease within 200±50 days. A preferred tagged PrP gene is MHu2M which contains the starting and terminating sequence of a mouse PrP gene and a non-terminal sequence region which is replaced with a corresponding human sequence which differs from a mouse PrP gene in a manner such that the protein expressed thereby differs at nine residues (MHu2M).

The term "genetic material related to prions" is intended to cover any genetic material which effects the ability of an animal to become infected with prions. Thus, the term encompasses any "PrP gene", "chimeric PrP gene", or "ablated PrP gene" which terms are defined herein as well as modification of such which effect the ability of an animal to become infected with prions.

The terms "host animal," "host non-human mammal," and the like are used to describe animals which will have their genome genetically and artificially manipulated so as to include genetic material which is not naturally present within the animal. For example, host animals include mice, hamsters and rats which have their PrP gene disrupted or altered by the insertion of a tagged artificial PrP gene of another animal or by the insertion of a tagged native PrP gene of a genetically diverse test animal.

The terms "ablated prion protein gene", "disrupted PrP gene", and the like are used interchangeably herein to mean an endogenous prion protein gene which has been altered (e.g., add and/or remove nucleotides) in a manner so as to render the gene inoperative. Examples of non-functional prion protein genes and methods of making such are disclosed in Büeler et al. (1992) Nature 356:577–582, which is incorporated herein by reference. One (heterozygous) or preferably both (homozygous) alleles of the genes are disrupted.

The terms "retaining the biological activity," "the biological activity of the naturally occurring protein or protein fragment", and the like, mean that the tagged protein or tagged protein fragment retains at least part of and preferably all of the characteristic biological activities and specificities of the unmodified, e.g., untagged, protein or protein fragment. For example, the FLAG-tagged chimeric Syrian hamster-mouse PrP (FLAG-MHM2PrP) retains the ability to support prion propagation in vivo when expressed in transgenic mice infected with Syrian hamster prions.

The terms "genetically diverse animal" and "genetically diverse mammal" are used to describe an animal which includes a native PrP codon sequence of the host animal which differs from the genetically diverse test animal by 17 or more codons, preferably 20 or more codons, and most preferably 28–40 codons. Thus, a mouse PrP gene is genetically diverse with respect to the PrP gene of a human cow or sheep, but is not genetically diverse with respect to the PrP gene of a hamster.

The terms "susceptible to infection" and "susceptible to infection by prions" and the like are used interchangeably herein to describe a transgenic animal of the invention which has an 80% or greater, preferably 98% or greater, and most preferably a 100% chance of developing a disease if inoculated with prions which would not normally infect a genetically diverse animal. Further, an animal "susceptible to infection" will develop symptoms of prion disease with 200±50 days or less after inoculation with prions which they are susceptible to being infected with.

The terms are used to describe a transgenic animal of the invention such as a transgenic mouse Tg(MHu2M) which, without the chimeric PrP gene, would rarely be susceptible to infection with a human or bovine prion (less than 20% chance of infection), but with the chimeric gene is susceptible to infection with human or bovine prions (80% to 100% chance of infection) and will show symptoms within 250 days or less after inoculation.

The term "incubation time" means the time from inoculation of an animal with a prion until the time when the animal first develops detectable symptoms of disease resulting from the infection. A reduced incubation time is one year or less, preferable about 200 days±50 days or less, more preferably about 50 days±20 days or less. Generally, in connection with the present invention, "incubation time" means the time from inoculation of an animal with any substance which causes a conformational change in a natural protein until that conformational change takes place in a detectable amount, e.g., detecting the exposed tag.

Epitope Tags

The invention includes epitope-tagged transgenes which are recombinant nucleic acid constructs encoding an amino acid sequence. The construct comprises a first sequence encoding biologically active protein or biologically active fragment and a second sequence coding for a tag with a heterologous epitope domain. The invention also includes transgenic animals expressing an epitope-tagged transgene. A variety of epitopes may be used to tag a protein, so long as the epitope (1) is heterologous to the naturally-occurring protein, and (2) the epitope-tagged protein retains at least part and preferably all of the biological activity of the unmodified protein. Such epitopes may be naturally-occurring amino acid sequences found in nature, artificially constructed sequences, or modified natural sequences. Recently, a variety of artificial epitope sequences have been described that have been shown to be useful for tagging and detecting recombinant proteins. One such tag, the eight amino acid FLAG marker peptide (Asp-Tyr-Lys-Asp-Asp-Asp-Asp-Lys) (SEQ ID NO:1), has a number of features which make it particularly useful for not only detection but also affinity purification of recombinant proteins (Brewer (1991) Bioprocess Technol. 2:239–266; Kunz (1992) J. Biol. Chem. 267:9101–9106). Inclusion of the FLAG epitope in recombinant proteins avoids the necessity for the development of a specialized scheme or functional assay for protein purification and circumvents need to raise antibodies against the tagged protein, the first four amino acids of this sequence comprising the antigenic site for α-FLAG M1 and M2 monoclonal antibodies. The small octapeptide has a high degree of hydrophilicity, thus maximizing accessibility to α-FLAG M1 and M2 monoclonal antibodies. A particularly useful feature is the calcium-dependent binding of the α-FLAG M1 monoclonal antibody to recombinant proteins containing the FLAG peptide. Removal of the $Ca^{2+}$ by chelation with EDTA allows for efficient immunoaffinity purification without denaturation. A further advantage of the FLAG system is that it allows cleavage of the FLAG peptide from purified protein since the tag contains the rare five amino acid recognition sequence for enterokinase. The anti-FLAG M1 antibody requires an N-terminal FLAG sequence. A second anti-FLAG monoclonal antibody (anti-FLAG M2) has been employed in immunoaffinity purification of N-terminal Met-FLAG and C-terminal FLAG fusion proteins (Brizzard et al. (1994) Biotechniques 16:730–735). This antibody has, however, been found to cross-react with a splicing isoform of $Mg^{2+}$ dependent protein phosphatase beta (MPP beta) which contains a sequence motif with five out of eight amino acid residues identical to the FLAG peptide (Schafer (1995) Biochem. Biophys. Res. Commun. 207:708–714). Binding of an anti-FLAG M2 monoclonal antibody to the FLAG epitope is not calcium-dependent, but bound fusion proteins can be eluted by competition with FLAG peptide.

Additional artificial epitope tags include an improved FLAG tag having the sequence Asp-Tyr-Lys-Asp-Glu-Asp-Asp-Lys (SEQ ID NO:2), a nine amino acid peptide sequence Ala-Trp-Arg-His-Pro-Gln-Phe-Gly-Gly (SEQ ID NO:3) referred to as the "Strep tag" (Schmidt (1994) J. Chromatography 676:337–345), poly-histidine sequences, e.g., a poly-His of six residues which is sufficient for binding to IMAC beads, an eleven amino acid sequence from human c-myc recognized by monoclonal antibody 9E10, or an epitope represented by the sequence Tyr-Pro-Tyr-Asp-Val-Pro-Asp-Tyr-Ala-Ile-Glu-Gly-Arg (SEQ ID NO:11) derived from an influenza virus hemagglutinin (HA) subtype, recognized by the monoclonal antibody 12CA5. Also, the Glu-Glu-Phe sequence recognized by the anti-α-tubulin monoclonal antibody YL1/2 has been used as an affinity tag for purification of recombinant proteins (Stammers et al. (1991) FEBS Lett. 283:298–302).

The present invention features transgenic animals having a transgene encoding a tagged protein or protein fragment. A variety of natural, modified, or artificial epitope tags may be used so long as insertion into the gene construct does not completely interfere with the biological activity of the encoded protein.

Natural and Chimeric PrP Gene

The present invention may be used to generate transgenic animals carrying a DNA construct encoding an epitope-tagged naturally occurring or chimeric PrP gene. Examples of naturally occurring PrP proteins are shown in FIGS. 1–3. PrP genes from any animal of interest may be epitope-tagged so long as the resulting tagged PrP molecule retains the biological activity of the natural protein, e.g., the ability of tagged $PrP^C$ to be converted into $PrP^{Sc}$ and to propagate prions.

Chimeric PrP transgenes are described in U.S. Pat. No. 5,565,186, issued Oct. 15, 1996, U.S. Pat. No. 5,763,740 issued Jun. 9, 1998, and U.S. Pat. No. 5,908,969 issued Jun. 1, 1999, all of which are herein specifically incorporated by reference, including the chimeric Syrian hamster/mouse (SHa/Mo) transgene MH2M which carries 5 amino acid substitutions found in SHaPrP lying between codons 94 and 188 (Scott et al. (1993) Cell 73:979–988), and the chimeric human/mouse PrP gene, MHu2M, in which the same region of the mouse gene is replaced by the corresponding human sequence which differs from the mouse PrP at 9 codons.

Mice expressing the MHu2M chimeric PrP transgene have been shown to be susceptible to human prions after abbreviated incubation times. That is, transgenic mice carrying the MHu2M gene [Tg(MHu2M)] will, after inoculation with human prions, develop disease symptoms attributed to the prions within about 180 days. Further, 80% or more of the transgenic mice inoculated with human prions will develop symptoms of the disease. Thus, PrP transgenic animals provide an excellent system for assessing prion infections.

Transgenic Animals

The invention features transgenic animals having a transgene encoding an amino acid sequence comprising a biologically active protein fragment and a heterologous epitope domain. Transgenic animals having a tagged protein transgene are generated by introducing the DNA constructs encoding the desired tagged protein into the germline DNA of a host animal. Several methods for generating transgenic animals are known in the art, see for example, Gordon et al. (1980) Proc. Natl. Acad. Sci. 77:7380–7384, herein specifically incorporated by reference for methods of genetically transforming embryos by microinjection of DNA). Introduction of the desired tagged protein sequences can also be accomplished by microinjection into a fertilized egg of the host animal; transformation of embryonic stem (ES) cells with the desired DNA and introduction of the transformed ES cells into host animal blastocysts; or embryonic transduction with a retroviral vector containing the desired transgene. Another method of generating transgenic animals is described in U.S. Pat. No. 5,487,992, which uses a positive-negative selector (PNS) vector for inserting a DNA sequence by homologous recombination into a target site in the host animal genome.

Generation of transgenic animals by microinjection techniques is well known in the art. To generate tagged protein transgenic mice, for example, a DNA fragment encoding the protein of interest into which the epitope tag has been inserted is prepared and microinjected into fertilized eggs of mice, followed by transfer of viable eggs into the oviducts of pseudopregnant mice (Hogan et al. (1986) *Manipulation of Mouse Embryos: A Laboratory Manual*, Cold Spring Harbor Laboratory, N.Y., herein specifically incorporated by reference for methods of generating transgenic animals).

In a preferred embodiment, transgenic animals are generated having a tagged PrP transgene. In a specific embodiment, the tagged PrP transgene is a PrP sequence tagged with the FLAG epitope at codon 22 (FIG. 5). Preferably, the transgenic animal is an animal which does not express the endogenous PrP gene. The transgenic mouse may be heterozygous or homozygous for modifications in one or both alleles resulting in effective deletion of the endogenous PrP gene (ΔPrP). Preferably, both alleles of the genes are disrupted. The endogenous prion protein gene may be altered in any manner (e.g., add and/or remove nucleotides) so as to render the gene inoperative. Examples of non-functional prion protein genes and methods of making such are disclosed in Büeler et al. (1992) Nature 356:577–582, which is incorporated herein by reference.

Expression of a Biologically Active Tagged PrP Protein

Previous efforts to generate a $MoPrP^C$ specific antibody have been unsuccessful, likely resulting from recognition of MoPrP as self in immunized animals. This limitation has now been overcome by tagging PrP with the FLAG epitope tag. The FLAG system has the advantage of efficient, one-step immunoaffinity purification without denaturation using the anti-FLAG M1 monoclonal antibody which binds to proteins containing the FLAG peptide in a calcium-dependent manner. Recognition of FLAG fusion proteins by the a-FLAG M1 monoclonal antibody relies on the location of the FLAG sequence at the N-terminus of the protein. Since PrP is processed in cells by the removal of a N-terminal signal peptide, the FLAG sequence was inserted distal to the signal peptidase cleavage site at amino acid residue 22 of PrP.

To construct FLAG-tagged PrP, a new recognition sequence for the restriction enzyme StuI was created upstream of the signal peptidase cleavage site which cuts PrP after amino acid 22. The unique StuI site was created by changing a T for an A at nucleotide position 57 of the MoPrP gene by the PCR-mediated mutagenesis described in Example 1 (FIG. 4). Variation at this nucleotide position do not change the predicted primary structure of PrP. Complementary oligonucleotide sequences [TTGGCCGCTTCT TGTCATCGTCGTCCTTGTAGTCGCAGA (SEQ ID NO:5) and CCTCTGCGACTACAAGGACGACGATGA-CAAGAAGAAGCGGCCAAAGC (SEQ ID NO:6)] were synthesized and used to replace the nucleotide sequences between the StuI and PflMI sites flanking the signal peptidase cleavage site. This reconstituted the C-terminal portion of the signal peptide and newly inserted the 8 amino acid FLAG sequence after this position (FIG. 5). The mature FLAG-tagged MoPrP differs from wild-type MoPrP by the inclusion of the 8 FLAG amino acids, with aspartate, the first amino acid of the FLAG sequence, being amino acid 23 at the N-terminus of the mature FLAG-tagged PrP. A second tagged PrP construct, FLAG-MHM2PrP, was engineered which also inserted the epitope for monoclonal antibody 3F4 derived from SHaPrP (Kascsak et al. (1987) J. Virol. 61:3688–3693) into MoPrP.

The FLAG-MHM2PrP construct was inserted into an MHM2PrP expression cassette previously described by Scott et al. (1992) Protein Sci. 1:986–997, cloned into the SPOX.II neo expression vector, and transfected into ScN2A cells (Example 2). Mouse neuroblastoma ScN2A cells which are chronically infected with mouse prions have been previously described (Butler et al. (1988) J. Virol. 62:1558–1564).

Neomycin-resistant colonies expressing recombinant PrP were selected in medium containing G418. Mouse PrP is not recognized by monoclonal antibody 3F4, so the inclusion of the 3F4 epitope allows for the discrimination between ectopically expressed PrP and endogenous MoPrP in the event that FLAG-MHM2PrP was not recognized by the anti-FLAG M1 monoclonal antibody.

Western blots of cell lysates from ScN2A cells expressing FLAG-MHM2 probed with monoclonal antibody 3F4 showed that inclusion of the FLAG epitope at amino acid 23 does not prevent expression of authentically processed PrP. The FLAG-MHM2PrP appears to be correctly glycosylated, but the apparent molecular weights of FLAG-MHM2PrP glycoforms are about 1–2 kDa greater than MHM2PrP. It is likely that this increase in molecular weight is due to the inclusion of the FLAG peptide in mature $PrP^C$ rather than aberrant processing at the signal peptidase cleavage site since the shifts in size compared to MHM2PrP are in agreement with the predicted molecular weight of the FLAG-PrP fusion protein.

Inclusion of the FLAG sequence into PrP between positions 22 and 23 does not interfere with the processing or biological activity of the tagged protein. The presence of the FLAG epitope did not inhibit proteolytic maturation of PrP at the signal peptidase cleavage site or normal processing and GPI anchorage of PrP at the cell surface. Evidence that the signal peptide is efficiently removed from FLAG-MHM2PrP comes from the immunoreactivity of the ectopically expressed PrP with not only the 3F4 monoclonal antibody but also the anti-FLAG M1 monoclonal antibody, the latter only recognizing fusion proteins with the FLAG tag at the N-terminus. Attempts to detect FLAG-MHM2PrP in transfected ScN2A cells using anti-FLAG M2 monoclonal antibody were unsuccessful. Inclusion of the FLAG tag also does not interfere with proteolytic cleavage at the C-terminus or attachment of PrP on the external surface of cells by GPI anchorage as demonstrated by release of FLAG-MHM2PrP from the cell surface by phosphatidylinositol-specific phospholipase C (PIPLC).

Since placement of the FLAG epitope was required at the N-terminus of mature PrP for recognition by the anti-FLAG M1 monoclonal antibody, it was unknown whether, even though FLAG-MHM2PrP is efficiently expressed and processed, the location of this hydrophilic sequence would interfere with the ability of recombinant PrP to support prion propagation, perhaps by affecting the ability of $PrP^C$ to adopt a conformation essential for the production of infectious prions. A hallmark of $PrP^{Sc}$ is its insolubility in detergents and relative protease resistance.

Proteinase K digestion of PrP in infected ScN2A cells results in the persistence of a core molecule referred to as PrP 27–30 consisting predominantly of amino acid residues 90 to 231. Immunoblotting with anti-FLAG M1 monoclonal antibody failed to detect PrP 27–30 derived from FLAG-MHM2PrP since the FLAG epitope at amino acid 23 is lost following treatment with proteinase K. Using the 3F4 monoclonal antibody to detect proteinase K-resistant FLAG-MHM2PrP, it was found that, like ScN2A cells expressing MHM2PrP, ScN2A cells expressing FLAG-MHM2PrP efficiently produced PrP 27–30. This phenomenon has also been demonstrated with a nine amino acid peptide sequence, consisting of Ala-Trp-Arg-His-Pro-Gln-Phe-Gly-Gly (SEQ ID NO:3) referred to as the "Strep tag" (Schmidt et al. (1994) supra) which behaves in the same way when inserted at the same location. These results establish that the addition of the amino acid sequences at this location of PrP does not interfere with its normal processing, and more importantly, does not interfere with its ability to be converted to the $PrP^{Sc}$ isoform.

The ability of FLAG-MoPrP expressed in transgenic mice to support prion infectivity was tested (Example 4). The FLAG-PrP sequence was engineered into a MoPrP expression cassette which was cloned into the cosSHa.tet cosmid expression vector for transgenic mouse production (Scott et al. (1992) Protein Scie. 1:986–997). Five transgenic founders were produced: three in FVB mice and two in FVB/Prn $p^{o/o}$ mice. FVB mice expresses endogenous MoPrP; FVB/Prn $p^{o/o}$ mice are a line of mice in which the ablated MoPrP gene has been repeatedly backcrossed to FBV and do not express endogenous MoPrP. To simplify analysis, high copy number founders derived only from microinjection of FVB/Prn $p^{o/o}$ embryos were selected for breeding since only transgene-expressed FLAG-MoPrP and not endogenous wild-type MbPrP is expressed in this case. Interference of transgene-directed prion propagation by endogenous wild-type MoPrP has been observed in other experiments (Telling et al. (1994) Proc. Natl. Acad. Sci. 91:9936–9940; Telling et al. (1995) supra). Using the polyclonal antibody R073, a rabbit polyclonal antibody raised against purified PrP 27–30 of hamster which also reacts with MoPrP, it was estimated by serial dilution and immunodotblotting, that the level of FLAG-MoPrP expression in brain extracts from one line, Tg(FLAG-MoPrP)FVB/Abl 7755, was about 100-fold higher than wild-type levels of MoPrP expression. The extremely high level of FLAG-$MoPrP^C$ expression meant that FLAG-tagged PrP was more readily detected in brain homogenates of Tg(FLAG-MoPrP) FVB/Abl 7755 mice by the anti-FLAG M1 monoclonal antibody than in ScN2A cells expressing FLAG-MHM2PrP.

Figure 6:
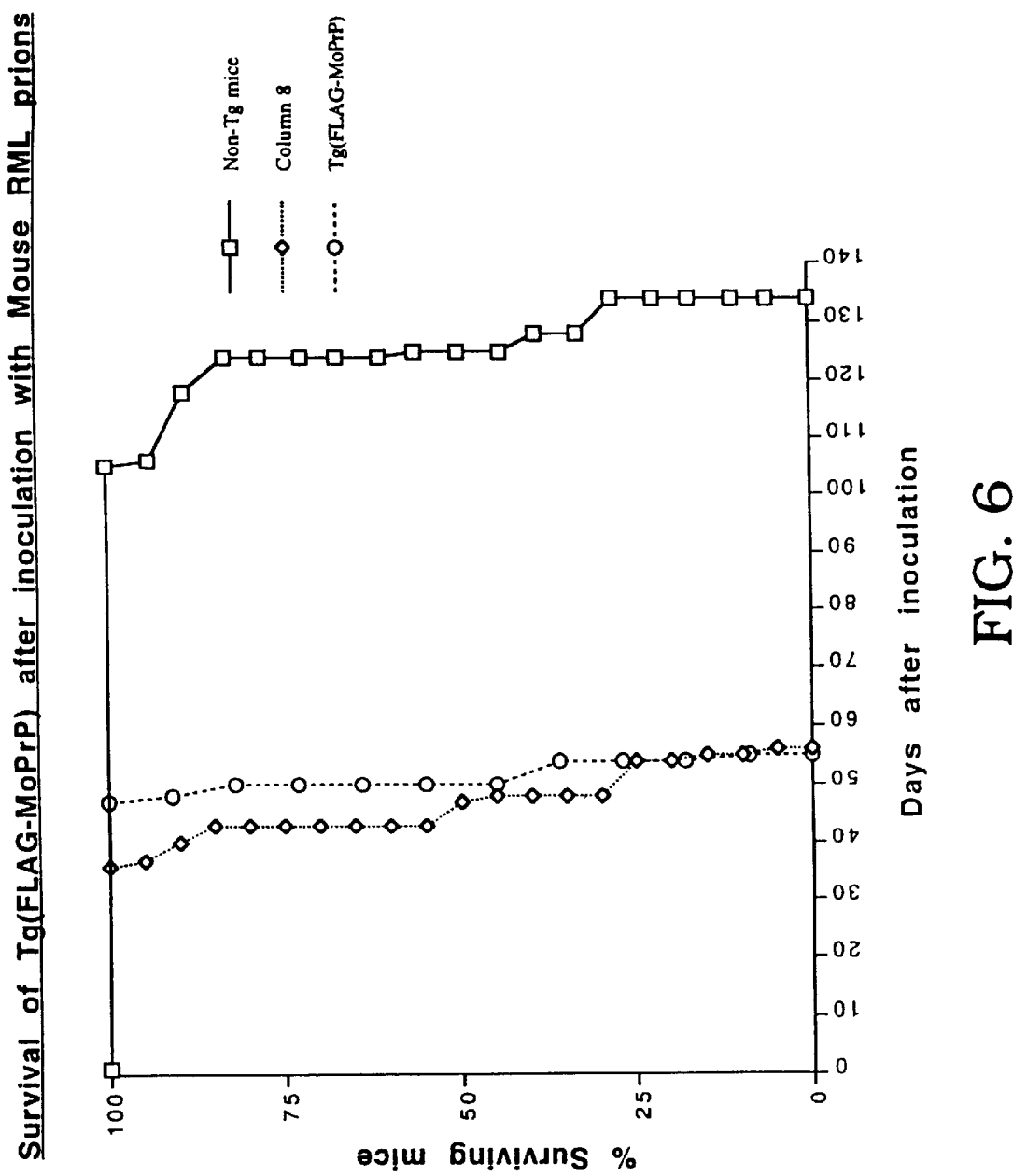
FIG. 6 is a chart showing the survival of Tg(FLAG-MoPrP) relative to non-transgenic mice ("Non-Tg mice") and a transgenic mouse line which overexpresses normal mouse PrP ("Tg(MoPrP-A)") after inoculation with mouse RML prions.

In order to determine if Tg(FLAG-MoPrP) mice supported replication of mouse prions, high copy number Tg(FLAG-MoPrP)FVB/Abl 7755 mice were inoculated intracerebrally with mouse RML prions (Example 5). RML is a specific mouse prion isolate derived from Chandler strain mice (Rocky Mountain Laboratory, Hamilton, Mont.). Inoculated mice developed clinical signs of scrapie with an average incubation time of about 52 days (FIG. 6). This is similar to incubation times observed in high copy number Tg(MoPrP)4053 mice, which over-express MoPrP about 8-fold higher than wild-type (Carlson et al. (1994) Proc. Natl. Acad. Sci. 91:5690–5694) and is considerably shorter than wild-type non-transgenic mice which have average incubation times of approximately 130 days.

Neuropathological features of the brains of clinically sick include, widespread vacuolation, particularly in the white matter, accompanied by reactive astrocytic gliosis. Hydrolytic autoclaving using polyclonal antibody R073 revealed the presence of PrP-containing plaques predominantly in the corpus callosum.

The brains of clinically sick Tg(FLAG-MoPrP)FVB/Abl 7755 mice inoculated with mouse RML prions contained proteinase K-resistant PrP 27–30 which was detectable using the R073 antibody. Proteinase K treatment results in the loss of the anti-FLAG M1 monoclonal antibody epitope at residue 23 so FLAG-$MoPrP^{Sc}$ is not detected with this antibody. Since these transgenic mice were derived from FVB/Prn-p$^{0/0}$ mice which express no endogenous MoPrP, the R073-reactive PrP$^{Sc}$ is derived exclusively from transgene-expressed FLAG-MoPrP. The level of FLAG-MoPrP$^{Sc}$ is about 2-fold lower than MoPrP$^{Sc}$ in inoculated wild-type mice. A similar reduction in MoPrP$^{Sc}$ levels is observed in short incubation time Tg(MoPrP)4045 mice which overexpress MoPrP.

Inclusion of the FLAG epitope in MoPrP facilitated the in situ detection of PrP$^C$ by histoblot analysis. FLAG-MoPrP$^C$, but not FLAG-MoPrP$^{Sc}$ was detected using the anti-FLAG M1 monoclonal antibody because the FLAG epitope is lost upon proteinase K digestion of PrP. The distribution of PrP$^C$ was found to be identical using either the anti-FLAG M1 monoclonal antibody or polyclonal R073 antibody. Tg(FLAG-MoPrP) mice inoculated with mouse RML prions revealed a distribution of FLAG-MoPrP$^{Sc}$ which was similar to MoPrP$^{Sc}$ in RML-inoculated wild-type mice.

Since the anti-FLAG M1 monoclonal antibody efficiently recognizes ectopically expressed MoPrP in Tg(FLAG-MoPrP) mice and the levels of FLAG-MoPrP expression were determined to be approximately 100-fold higher than wild-type MoPrP expression, Tg(FLAG-MoPrP)FVB/Abl 7755 is expected to be an excellent source for large amounts of FLAG-MoPrP$^C$. The presence of the epitope tag allows the tagged PrP molecule to be obtained in high purity under non-denaturing conditions by a one-step immunoaffinity chromatography procedure. Recently, an improved FLAG tag has been generated in which the fifth amino acid of the FLAG sequence was changed from an aspartate residue to a glutamate residue. The binding affinity of the M1 antibody was increased six-fold in Western blots over the original FLAG sequence (Knappik (1994) Biotechniques 17:754–761). This raises the possibility that transgenic mice expressing PrP with the improved FLAG tag may be an even better source of recombinant material in the future.

Use of Epitope Placement to Distinguish Between Protein Isoforms

The epitope-tagging system may also be used to used to differentiate between the conformational shapes of a protein. For example, the epitope tag may be placed in a protein such that the epitope is exposed in one conformational shape and buried in another.

Epitope placement is compared with both epitope-tagged isoforms of MoPrP, HuPrP and MHu2MPrP to locate a placement of the artificial epitope in the protein which results in the exposure of the epitope in the PrP$^{Sc}$ conformational shape and epitope burial in the interior of the PrP$^C$ conformational shape (Example 6). Such tagging approaches are useful in an assay to,distinguish between infectious and non-infectious isoforms of PrP. For example, certain regions between residues 109–141 are expected to change from a helix-loop-helix structure into a β-sheet organization. This is expected to change the pattern of presentation of the side chains of these residues so that epitopes that are exposed in the α-helical PrP$^C$ isoform are sequestered in the β-sheet-rich PrP$^{Sc}$ isoform, and vice versa. The exposure of tags placed within this region should be influenced by the conformation change between PrP$^C$ and PrP$^{Sc}$.

Use of Epitope Tagging to Isolate Replication Intermediates

The epitope tagging technique may be used to isolate "replication intermediates" composed of PrP$^C$, PrP$^{Sc}$, and protein(s) X from ScN2A cells or scrapie-infected mouse brain. FLAG-tagged complexes are immunoprecipitated with anti-FLAG antibodies in the presence of buffer containing low levels of detergent to minimize nonspecific binding and the immunoprecipitates recovered by centrifugation. Proteins from these tagged complexes are released by chelation of the metal ions and analyzed by SDS-PAGE and Western blot. Non-PrP molecules are subjected to N-terminal sequencing leading to the identification of molecular clones encoding such proteins.

This approach of isolating complexes of PrP$^C$, PrP$^{Sc}$ and protein(s) X has the distinct advantage of being directed at detecting a ternary complex of the three proteins. Complexes of PrP$^C$ or PrP$^{Sc}$ with other proteins may also be detected. This is important for the reconstitution of an ex vivo/in vitro assays for PrP replication.

EXAMPLES

The following examples are put forth so as to provide those of ordinary skill in the art with a complete disclosure and description of how to make and use various constructs and perform the various methods of the present invention and are not intended to limit the scope of what the inventors regard as their invention. Unless indicated otherwise, parts are parts by weight, temperature is in degrees centigrade, and pressure is at or near atmospheric pressure. Efforts have been made to ensure accuracy with respect to numbers used, (e.g., length of DNA sequences, molecular weights, amounts, particular components, etc.) but some deviations should be accounted for.

Example 1

Construction of Epitope-Tagged PrP Expression Cassettes

To construct FLAG-tagged PrP expression cassettes, a new recognition sequence for the restriction enzyme StuI was created upstream of the signal peptidase sequence at amino acid 22 (FIG. 4). The StuI site was created by changing a T for an A at nucleotide position 57 in a subclone of the MoPrP gene extending from the start site of the open reading frame to the Kpn1 site at nucleotide position 277. This was achieved by PCR-mediated mutagenesis in which one of the primers for the reaction contained a mismatch (SEQ ID NO:13): 5'-CCCTCCAGGCTTTGGCCGCTT CTTGCAGAGGCCTACATCAGT-3'.

Complementary 42 and 47 oligonucleotides sequences were synthesized and annealed [(SEQ ID NO:5)(SEQ ID NO:6)]. The nucleotide sequence reconstituted the distal portion of the signal peptide and the signal peptidase cleavage site, followed by the 8 amino acid FLAG sequence and proximal sequence of mature PrP (FIG. 5). This FLAG-tagged sequence was subcloned into two different PrP expression cassettes: MoPrP to produce the FLAG-MoPrP cassette for transgenic mouse production and FLAG-MHM2PrP for expression in cultured cells.

Example 2

FLAG-tagged PrP is Authentically Expressed and is a Substrate for PrP$^{Sc}$ Production in Cultured ScN2A Cells The FLAG-MHM2PrP expression cassette was cloned into the SPOX.II neo expression vector (Scott et al. (1992) Protein Sci. 1:986–997) which allows for direct selection of neomycin resistant transfected cells by growth in medium containing G418. Mouse neuroblastoma N2A cells chronically infected with mouse prions (ScN2A cells) were grown in 6-well plates and transformed to neomycin resistance by transfection with SPOX-based FLAG-MHM2PrP or control MHM2PrP constructs by DOTAP-mediated transfection (Boehringer Mannheim Biochemicals) and growth in G418-containing medium. Neomycin resistant colonies became apparent approximately 2 weeks after transfection, and these colonies were pooled and passaged.

When stable cultures were established, NP-40 detergent lysates were isolated from either FLAG-MHM2PrP or control MHM2PrP-expressing cells and used for immunoblot analysis. In some experiments, PIPLC was included in the culture medium and PrP cleaved from the cell membrane by the treatment was purified by methanol precipitation and centrifugation.

Analysis of protease-resistant FLAG-MHM2PrP or MHM2PrP in stable cell lines was accomplished by digesting a 1 ml aliquot of cell lysate derived from a confluent 100 mm dish with proteinase K at a concentration of 20 µg/ml for 1 hour at 37° C. Detergent-resistant, proteinase K-resistant proteins were purified by centrifugation at 40,000×g for 1 hour and the pellets resuspended in 20 µl lysis buffer (150 mM NaCl, 10 mM Tris, pH 7.5, 0.5% NP-40, 0.5% deoxycholate). Digested or undigested cell lysates were added to an equal volume of 2× SDS-PAGE sample buffer and processed for SDS-PAGE analysis. In all cases, immunoblotting was performed using anti-PrP monoclonal antibody 3F4 directed against hamster $PrP^{Sc}$ (Kascsak et al. (1987) J. Virol. 61:3688–3693).

Example 3

Transgenic Mice Expressing FLAG-Tagged PrP

The FLAG-MoPrP ORF expression cassette is flanked by SalI and XhoI, which cleave immediately adjacent to the initiation and termination codons of the PrP ORF, respectively. This allowed for convenient subcloning into the cos.SHaTet expression vector (Scott et al. (1992) Protein Sci. 1:986–997) to produce the cos.SHaTet FLAG-MoPrP clone. The isolation and screening of recombinant cosmid clones have been described (Scott et al. (1993) Cell 73:979–988, herein specifically incorporated by reference for procedures related to the isolation and screening of recombinant cosmid clones). After verification of the predicted nucleotide sequences of the FLAG-MoPrP ORF, the cosmid NotI fragment, recovered from large scale DNA preparations, was used for microinjections into the pronuclei of fertilized FVB/N or FVB/Prn $p^{0/0}$ mouse embryos as described (Scott et al. (1989) Cell 59:847–857; Scott et al. (1992) supra, each of which is herein specifically incorporated by reference for procedures for generating transgenic animals).

Five transgenic founders were produced: three in FVB mice and two in FVB/Prn $p^{0/0}$ mice. Genomic DNA, isolated from tail tissue of weanling animals, was screened for the presence of incorporated transgenes using probes that hybridize to the 3'-untranslated region of the SHaPrP gene contained in the cosSHa.Tet vector (Scott et al. (1992) supra). By comparing the hybridization signals of the DNA from weanling mice with standardized DNA samples, it was estimated that one line, Tg(FLAG-MoPrP)FVB/Abl 7755, had transgene copy numbers in excess of approximately 60 transgene copies per cell. Using the polyclonal antibody, RO73, it was estimated by serial dilution and immunoblotting, that the level of FLAG-MoPrP expression in brain extracts from the Tg(FLAG-MoPrP)FVB/Abl 7755 line was approximately 100-fold higher than wild-type levels of MoPrP expression.

Example 4

Tg(FLAG-MoPrP) Mice Support Replication of Mouse Prions

The RML isolate from Swiss mice (Chandler (1961) Lancet 1:1378–1379) was passaged in Swiss mice from a closed colony at the Rocky Mountain Laboratory (Hamilton, Mont.) or in Swiss CD-1 mice obtained from Charles River Laboratories (Wilmington, Mass.). Mice were inoculated intracerebrally with 30 µl of brain extract using a 27 gauge needle inserted into the right parietal lobe. Beginning 30 days after inoculation, mice were examined for neurologic dysfunction every 3 days. When clinical signs of CNS dysfunction appeared, the mice were examined daily. To confirm the clinical diagnosis, the brains of some animals whose death was obviously imminent were taken for histopathological studies.

Brains were dissected rapidly after sacrifice of the animal and immersion fixed in 10% buffered formalin. The tissue was embedded in paraffin and 8 µm thick histological sections were prepared for staining by the hematoxylin and eosin method and peroxidase immunohistochemical method for glial fibrillary acidic protein and PrP as described previously (DeArmond et al. (1987) Neurology 37:1271–1280; Scott et al. (1989) supra). Histoblots for localization of $PrP^C$ or protease-resistant PrP were made by pressing 16 mm thick unfixed cryostat sections of brain to nitrocellulose paper as previously described (Taraboulos (1992) Proc. Natl. Acad. Sci. 89:7620–7624). To localize $PrP^{Sc}$, the histoblot was exposed to 400 µg/ml proteinase K for 18 hours at 37° C. to eliminate $PrP^C$, exposed to 3 M guanidinium thiocyanate to denature the remaining $PrP^{Sc}$, followed by immunostaining with PrP specific-antibody RO73 or anti-FLAG M1 monoclonal antibody.

Example 5

Immunopurification of FLAG-MoPrP From Tg (FLAG-MoPrP) Mice

The brain of an uninoculated Tg(FLAG-MoPrP)FVB/Abl 7755 mouse was homogenized in TBS/10 mM CaCl and NP-40 detergent was added to 0.1%. The preparation was applied to a 5 ml column bed comprising anti-FLAG M1 monoclonal antibody coupled to agarose beads. The flow-through was reapplied repeatedly to ensure optimal binding. The column bed was washed three times with 15 ml TBS/Ca. Bound FLAG-MoPrP was eluted with TBS containing 2 mM EDTA which was applied in eight 1 ml aliquots for 10 min each.

Example 6

Use of Epitope Tag to Distinguish Protein Conformational Shapes

The placement of epitope tags at various positions in the prion protein is accomplished by generating recombinant PrP gene sequences harboring the DNA sequence for the epitope at different locations. The working model of $PrP^C$ is the four helix bundle model proposed by Huang et al. L(1994) Proc. Natl. Acad. Sci. 91:7139–7143. Epitopes are engineered at regions of proposed α-helical structure, which are believed to change conformation during prion replication, or in the loop region connecting the α-helices.

The epitope-tagged sequences are engineered using standard recombinant procedures. The host PrP molecule, MHM2PrP, allows detection by the 3F4 monoclonal antibody (Kascsak et al. (1987) J. Virol. 61:3688–3693) by including the hamster-derived epitope recognized by 3F4. These recombinant PrP constructs are transfected into ScN2A cells which are chronically infected with mouse prions, (Butler et al. (1988) J. Virol. 62:1558–1564). Detection of the ectopically expressed construct is facilitated by 3F4 or by antibodies directed against the heterologous epitope. PrP$^{Sc}$ is detected with 3F4 after digestion with prdteinase K. Detection of PrP$^{Sc}$ by 3F4 demonstrates that inclusion of the epitope tag at particular locations does not interfere with PrP$^C$ conversion. Ideally, antibody directed against the epitope tag would detect only PrP$^{Sc}$, not PrP$^C$, because in the latter conformation the epitope would be buried and inaccessible to the antibody. After determination of the ideal location for placement of the epitope tag, transgenic mice expressing PrP with the epitope tag at the desired location are made and infected with prions. Epitope-tagged PrP$^{Sc}$ and PrP$^C$ are isolated from the brains of the transgenic mice using standard procedures. Low resolution analytical techniques such as circular dichroism and infrared spectroscopy are used to determine that the PrP$^{Sc}$ isoform detected by anti-epitope antibody is of the β-sheet conformation, and the PrP$^C$ isoform is of the α-helical conformation.

The instant invention is shown and described herein in what is considered to be the most practical, and preferred embodiments. It is recognized, however, that departures may be made therefrom which are within the scope of the invention, and that modifications will occur to one skilled in the art upon reading this disclosure.

What is claimed is:

1. A recombinant nucleic acid construct comprising:
a first nucleic acid sequence encoding a PrP protein; and
a second nucleic acid sequence encoding a heterologous epitope domain;
wherein the PrP protein has two different three dimensional conformations, a first $PrP^C$ and a second $PrP^{Sc}$ conformation, wherein the heterologous epitope domain is spatially positioned within the PrP protein such that the epitope domain is at least 20% more exposed in the second conformation relative to the first conformation.

2. The construct of claim 1, wherein the PrP protein is a human PrP protein.

3. The construct of claim 1, wherein the PrP protein is selected from the group consisting of a natural, synthetic, and chimeric PrP protein.

4. The construct of claim 1, wherein the heterologous epitope domain is a peptide selected from the peptide group of FLAG, Strep, poly-histidine, human c-myc peptide recognized by monoclonal antibody 9E10, hemagglutinin peptide recognized by monoclonal antibody 12CA5, and Glu-Glu-Phe.

5. The construct of claim 4, wherein said FLAG peptide has a sequence Asp-Tyr-Lys-AspAsp-Asp-Asp-Lys (SEQ ID NO:1) or Asp-Tyr-Lys-Asp-Glu-Asp-Asp-Lys (SEQ ID NO:2).

6. The construct of claim 4, wherein said Strep peptide has the sequence Ala-Trp-Arg-HisPro-Gln-Phe-Gly-Gly (SEQ ID NO:3).

7. The construct of claim 4, wherein said poly-histidine peptide has the sequence His-HisHis-His-His-His (SEQ ID NO:4).

8. The construct of claim 4, wherein said c-myc peptide has the sequence Glu-Gln-LysLeu Leu-Ser-Glu-Glu-Asp-Leu-Asn (SEQ ID NO:12).

9. The construct of claim 4, wherein said hemagglutinin peptide has the sequence Tyr-ProTyr-Asp-Val-Pro-Asp-Tyr-Ala-Ile-Glu-Gly-Arg (SEQ ID NO: 11).

10. The construct of claim 1, wherein the PrP protein has a heterologous FLAG epitope domain inserted before amino acid residue 23 of the PrP sequence, wherein said amino acid residue of the PrP protein corresponds to amino acid residue 23 of mouse PRP (SEQ ID NO: 7).

11. A cell line having operatively inserted therein a recombinant nucleic acid construct comprising:

a first nucleic acid sequence encoding a PrP protein; and a second nucleic acid sequence encoding a heterologous epitope domain;

wherein the PrP protein has two different three dimensional conformations, a first $PrP^{C}$ and a second $PrP^{Sc}$ conformation, wherein the heterologous epitope domain is spatially positioned within the PrP protein such that the epitope domain is at least 20% more exposed in the second conformation relative to the first conformation.

12. An assay for detecting infections prior material, said assay comprising the steps of:
   a) generating a cell line expressing an epitome tagged PrP protein, said cell line having an operatively inserted therein a recombinant nucleic acid construct comprising:
      a first nucleic acid sequence encoding a PrP protein; and
      a second nucleic acid sequence encoding a heterologous epitope domain;
      wherein the PrP protein has two different three dimensional conformations, a first $PrP^C$ and a second $PrP^{Sc}$ conformation, wherein the heterologous epitope domain is spatially positioned within the PrP protein such that the epitope domain is at least 20% more exposed in the second conformation relative to the first conformation;
   b) inoculating said cell with material containing infectious prion protein; and
   c) detecting the presence of epitope-tagged $PrP^{Sc}$ with an antibody that binds to the heterologous epitope.

13. The assay of claim 12, wherein said PrP protein is a cow protein, and the inoculating material is from a cow.

14. The assay of claim 12, wherein said PrP protein is a chimer cow/mouse protein, and the inoculating material is from a cow.

15. The assay of claim 12, wherein said PrP protein is a human protein, and the inoculating material is from a human.

16. The assay of claim 12, wherein said PrP protein is a chimeric human/mouse protein, and the inoculating material is from a cow.

17. The assay of claim 12, wherein said PrP protein is a sheep protein, and the inoculating material is from a cow.

18. The assay of claim 12, wherein said PrP protein is a chimeric sheep/mouse protein, and the inoculating material is from a cow.

* * * * *